(12) United States Patent
Dewey et al.

(10) Patent No.: US 11,517,443 B2
(45) Date of Patent: Dec. 6, 2022

(54) DUAL WEDGE EXPANDABLE IMPLANT, SYSTEM AND METHOD OF USE

(71) Applicant: Warsaw Orthopedic, Inc., Warsaw, IN (US)

(72) Inventors: Jonathan M. Dewey, Memphis, TN (US); Bertrand Peultier, Les Hopitaux Neufs (FR); Loic Josse, Collierville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/331,058

(22) Filed: May 26, 2021

(65) Prior Publication Data
US 2022/0133496 A1     May 5, 2022

Related U.S. Application Data

(63) Continuation-in-part of application No. 17/123,889, filed on Dec. 16, 2020.

(51) Int. Cl.
   *A61F 2/44*     (2006.01)
   *A61F 2/46*     (2006.01)
   *A61F 2/30*     (2006.01)

(52) U.S. Cl.
   CPC .. *A61F 2/4425* (2013.01); *A61F 2002/30433* (2013.01); *A61F 2002/30604* (2013.01); *A61F 2002/443* (2013.01)

(58) Field of Classification Search
   CPC ........ A61F 2/4425; A61F 2/44; A61F 2/4455; A61F 2/4611; A61F 2002/30433; A61F 2002/30604; A61F 2002/443

(Continued)

(56) References Cited

U.S. PATENT DOCUMENTS

| 4,401,112 A | 8/1983 | Rezaian |
| 4,553,273 A | 11/1985 | Wu |

(Continued)

FOREIGN PATENT DOCUMENTS

| CN | 107 137 166 A | 9/2017 |
| DE | 44 16 605 C1 | 6/1995 |

(Continued)

OTHER PUBLICATIONS

International Search Report, and Written Opinion for Application. No. PCT/US2019/019067, dated June 3, 2019.

(Continued)

*Primary Examiner* — Jessica Weiss
(74) *Attorney, Agent, or Firm* — Fox Rothschild LLP; Paul Marshall Ticer

(57) ABSTRACT

An expandable implant movable between a contracted position and an expanded position, is disclosed. In various embodiments, the implant may be defined by a superior endplate and an inferior endplate having proximal ramps and distal ramps disposed on an interior surface thereof, respectively. In various embodiments, a proximal set screw and a distal set screw may be independently coupled to a proximal wedge and a distal wedge. Upon rotation of the proximal set screw, the proximal wedge may act against the proximal ramps of the superior and inferior endplates and cause the implant to expand at the proximal end. Upon rotation of the distal set screw, the distal wedge may act against the distal ramps of the superior and inferior endplates and cause the implant to expand at the distal end. In some embodiments, both the superior and distal set screws may be rotated simultaneously.

20 Claims, 36 Drawing Sheets

(58) Field of Classification Search
USPC .......................................... 623/17.11–17.16
See application file for complete search history.

(56) References Cited

U.S. PATENT DOCUMENTS

| | | |
|---|---|---|
| 4,636,217 A | 1/1987 | Ogilvie et al. |
| 4,716,894 A | 1/1988 | Lazzeri et al. |
| 4,759,769 A | 7/1988 | Hedman et al. |
| 5,059,193 A | 10/1991 | Kuslich |
| 5,171,278 A | 12/1992 | Pisharodi |
| 5,228,811 A | 7/1993 | Potter |
| 5,284,483 A | 2/1994 | Johnson et al. |
| 5,336,223 A | 8/1994 | Rogers |
| 5,390,683 A | 2/1995 | Pisharodi |
| 5,522,899 A | 6/1996 | Michelson |
| 5,554,191 A | 9/1996 | Lahille et al. |
| 5,575,790 A | 11/1996 | Chen et al. |
| 5,609,635 A | 3/1997 | Michelson |
| 5,653,762 A | 8/1997 | Pisharodi |
| 5,653,763 A | 8/1997 | Errico et al. |
| 5,658,336 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,391 A | 12/1997 | Lin |
| 5,702,453 A | 12/1997 | Rabbe et al. |
| 5,702,455 A | 12/1997 | Saggar |
| 5,797,918 A | 8/1998 | McGuire et al. |
| 5,800,550 A | 9/1998 | Sertich |
| 5,865,848 A | 2/1999 | Baker |
| 5,893,890 A | 4/1999 | Pisharodi |
| 5,931,777 A | 8/1999 | Sava |
| 5,941,885 A | 8/1999 | Jackson |
| 5,971,987 A | 10/1999 | Huxel et al. |
| 5,980,522 A | 11/1999 | Koros et al. |
| 6,045,579 A | 4/2000 | Hochshuler et al. |
| 6,074,343 A | 6/2000 | Nathanson et al. |
| 6,080,193 A | 6/2000 | Hochshuler et al. |
| 6,099,531 A | 8/2000 | Bonutti |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,132,465 A | 10/2000 | Ray et al. |
| 6,159,211 A | 12/2000 | Boriani et al. |
| 6,159,244 A | 12/2000 | Suddaby |
| 6,176,882 B1 | 1/2001 | Biedermann et al. |
| 6,179,873 B1 | 1/2001 | Zientek |
| 6,190,414 B1 | 2/2001 | Young et al. |
| 6,193,757 B1 | 2/2001 | Foley et al. |
| 6,217,579 B1 | 4/2001 | Koros |
| 6,245,108 B1 | 6/2001 | Biscup |
| 6,309,421 B1 | 10/2001 | Pisharodi |
| 6,342,074 B1 | 1/2002 | Simpson |
| 6,371,989 B1 | 4/2002 | Chauvin et al. |
| 6,395,031 B1 | 5/2002 | Foley et al. |
| 6,423,063 B1 | 7/2002 | Bonutti |
| 6,432,106 B1 | 8/2002 | Fraser |
| 6,436,140 B1 | 8/2002 | Liu et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,491,724 B1 | 12/2002 | Ferree |
| 6,520,991 B2 | 2/2003 | Huene |
| 6,520,993 B2 | 2/2003 | James et al. |
| 6,524,238 B2 | 2/2003 | Velikaris et al. |
| 6,527,803 B1 | 3/2003 | Crozet et al. |
| 6,562,074 B2 | 5/2003 | Gerbec et al. |
| 6,576,016 B1 | 6/2003 | Hochshuler et al. |
| 6,623,525 B2 | 9/2003 | Ralph et al. |
| 6,629,998 B1 | 10/2003 | Lin |
| 6,635,086 B2 | 10/2003 | Lin |
| 6,648,917 B2 | 11/2003 | Gerbec et al. |
| 6,676,703 B2 | 1/2004 | Biscup |
| 6,685,742 B1 | 2/2004 | Jackson |
| 6,723,126 B1 | 4/2004 | Berry |
| 6,770,096 B2 | 8/2004 | Bolger et al. |
| 6,773,460 B2 | 8/2004 | Jackson |
| 6,821,298 B1 | 11/2004 | Jackson |
| 6,835,206 B2 | 12/2004 | Jackson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,923,814 B1 | 8/2005 | Hildebrand et al. |
| 6,926,737 B2 | 8/2005 | Jackson |
| 6,953,477 B2 | 10/2005 | Berry |
| 6,964,687 B1 | 11/2005 | Bernard et al. |
| 6,974,480 B2 | 12/2005 | Messerli et al. |
| 6,984,234 B2 | 1/2006 | Bray |
| 7,112,222 B2 | 9/2006 | Fraser et al. |
| 7,135,043 B2 | 11/2006 | Nakahara et al. |
| 7,137,997 B2 | 11/2006 | Paul |
| 7,172,627 B2 | 2/2007 | Fiere et al. |
| 7,188,626 B2 | 3/2007 | Foley et al. |
| 7,204,853 B2 | 4/2007 | Gordon et al. |
| 7,232,464 B2 | 6/2007 | Mathieu et al. |
| 7,238,203 B2 | 7/2007 | Bagga et al. |
| 7,255,700 B2 | 8/2007 | Kaiser et al. |
| 7,316,532 B2 | 1/2008 | Matthys-Mark |
| 7,316,714 B2 | 1/2008 | Gordon et al. |
| 7,407,483 B2 | 8/2008 | Perez-Cruet et al. |
| 7,481,766 B2 | 1/2009 | Lee et al. |
| 7,491,168 B2 | 2/2009 | Raymond et al. |
| 7,537,565 B2 | 5/2009 | Bass |
| 7,618,456 B2 | 11/2009 | Mathieu et al. |
| 7,625,394 B2 | 12/2009 | Molz, IV et al. |
| 7,637,909 B2 | 12/2009 | Lechot et al. |
| 7,655,046 B2 | 2/2010 | Dryer et al. |
| 7,678,148 B2 | 3/2010 | Peterman |
| 7,703,727 B2 | 4/2010 | Selness |
| 7,708,778 B2 | 5/2010 | Gordon et al. |
| 7,708,779 B2 | 5/2010 | Edie et al. |
| 7,727,280 B2 | 6/2010 | McLuen |
| 7,753,958 B2 | 7/2010 | Gordon et al. |
| 7,780,594 B2 | 8/2010 | Hutton |
| 7,806,932 B2 | 10/2010 | Webb et al. |
| 7,815,682 B1 | 10/2010 | Peterson et al. |
| 7,819,801 B2 | 10/2010 | Miles et al. |
| 7,824,428 B2 | 11/2010 | Mikkonen et al. |
| 7,828,849 B2 | 11/2010 | Lim |
| 7,846,167 B2 | 12/2010 | Garcia et al. |
| 7,846,207 B2 | 12/2010 | Lechmann et al. |
| 7,850,731 B2 | 12/2010 | Brittan et al. |
| 7,850,733 B2 | 12/2010 | Baynham et al. |
| 7,862,616 B2 | 1/2011 | Lechmann et al. |
| 7,875,076 B2 | 1/2011 | Mathieu et al. |
| 7,892,173 B2 | 2/2011 | Miles et al. |
| 7,909,869 B2 | 3/2011 | Gordon et al. |
| 7,914,559 B2 | 3/2011 | Carls et al. |
| 7,967,821 B2 | 6/2011 | Sicvol et al. |
| 7,981,031 B2 | 7/2011 | Frasier et al. |
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |
| 8,262,570 B2 | 9/2012 | White et al. |
| 8,262,662 B2 | 9/2012 | Beardsley et al. |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |

(56) References Cited

U.S. PATENT DOCUMENTS

| | | |
|---|---|---|
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Amin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 * | 10/2016 | Weiman ............... A61F 2/4455 623/17.16 |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 * | 11/2016 | Wagner ............... A61F 2/447 623/17.16 |
| 9,492,289 B2 | 11/2016 | Davenport et al. |

(56) References Cited

U.S. PATENT DOCUMENTS

| | | |
|---|---|---|
| 9,498,349 B2 | 11/2016 | Patterson et al. |
| 9,510,954 B2 | 12/2016 | Glerum et al. |
| 9,517,098 B2 | 12/2016 | Anderson |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Amin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |

(56) References Cited

U.S. PATENT DOCUMENTS

| | | |
|---|---|---|
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Tyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |
| 10,874,522 B2 | 12/2020 | Weiman |
| 10,874,523 B2 | 12/2020 | Weiman et al. |
| 10,874,524 B2 | 12/2020 | Bjork |
| 10,881,524 B2 | 1/2021 | Eisen et al. |
| 10,881,531 B2 | 1/2021 | Berry |
| 10,888,431 B1 | 1/2021 | Robinson |
| 10,898,344 B2 | 1/2021 | Alheidt et al. |
| 10,898,346 B1 | 1/2021 | Suddaby |
| 10,925,656 B2 | 2/2021 | Cole et al. |
| 10,925,750 B2 | 2/2021 | Zappacosta et al. |
| 10,925,752 B2 | 2/2021 | Weiman |
| 10,932,920 B2 | 3/2021 | Dewey et al. |
| 10,940,014 B2 * | 3/2021 | Greenhalgh .......... A61F 2/4405 623/17.16 |
| 10,945,858 B2 | 3/2021 | Bechtel et al. |
| 10,952,866 B2 | 3/2021 | Warren et al. |
| 10,959,855 B2 | 3/2021 | Miller et al. |
| 10,959,856 B2 | 3/2021 | Seifert et al. |
| 10,973,649 B2 | 4/2021 | Weiman et al. |
| 10,973,650 B2 | 4/2021 | Stein |
| 10,980,642 B2 | 4/2021 | Glerum et al. |
| 10,980,644 B2 | 4/2021 | Purcell et al. |
| 10,993,814 B2 | 5/2021 | Wolters |
| 11,007,067 B2 | 5/2021 | Masson et al. |
| 11,013,617 B2 | 5/2021 | Weiman et al. |
| 11,020,238 B2 | 6/2021 | Nichols et al. |
| 11,020,239 B2 | 6/2021 | Miller et al. |
| 11,026,804 B2 | 6/2021 | Jimenez et al. |
| 11,026,812 B2 | 6/2021 | Daffinson et al. |
| 11,033,401 B2 | 6/2021 | Shoshtaev |
| 11,033,402 B2 | 6/2021 | Melkent et al. |
| 11,033,404 B2 | 6/2021 | Faulhaber |
| 11,039,935 B2 | 6/2021 | McAfee |

(56) References Cited

U.S. PATENT DOCUMENTS

| | | |
|---|---|---|
| 11,045,326 B2 | 6/2021 | Seifert et al. |
| 11,045,327 B2 | 6/2021 | Nichols et al. |
| 11,051,949 B2 | 7/2021 | Walker et al. |
| 11,051,951 B2 | 7/2021 | Robinson et al. |
| 11,058,469 B2 | 7/2021 | Mahajan et al. |
| 11,065,127 B1 | 7/2021 | Lentner et al. |
| 11,065,129 B2 | 7/2021 | Sandul |
| 11,065,130 B2 | 7/2021 | Branch et al. |
| 11,076,966 B2 | 8/2021 | Faulhaber |
| 11,083,584 B2 | 8/2021 | Lauf et al. |
| 11,083,595 B2 | 8/2021 | Robinson |
| 11,090,167 B2 | 8/2021 | Emerick et al. |
| 11,096,795 B2 | 8/2021 | Padovani et al. |
| 11,096,797 B2 | 8/2021 | Moskowitz et al. |
| 11,103,366 B2 | 8/2021 | Glerum et al. |
| RE48,719 E | 9/2021 | Suddaby et al. |
| 11,109,980 B2 | 9/2021 | Seifert et al. |
| 11,116,644 B2 | 9/2021 | Marrocco et al. |
| 11,123,198 B2 | 9/2021 | Black et al. |
| 11,123,200 B2 | 9/2021 | Faulhaber |
| 11,129,731 B2 | 9/2021 | Miller et al. |
| 11,135,071 B2 | 10/2021 | Dewey et al. |
| 11,147,680 B2 | 10/2021 | Tyber et al. |
| 11,154,404 B2 | 10/2021 | Freedman et al. |
| 11,160,666 B2 | 11/2021 | Burkhardt et al. |
| 11,160,669 B2 | 11/2021 | Rogers et al. |
| 11,166,826 B2 | 11/2021 | Huang |
| 11,173,044 B1 | 11/2021 | Jones et al. |
| 11,179,234 B2 | 11/2021 | Dacosta et al. |
| 2002/0045943 A1 | 4/2002 | Uk |
| 2002/0045945 A1 | 4/2002 | Liu et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2003/0050701 A1 | 3/2003 | Michelson |
| 2003/0130739 A1 | 7/2003 | Gerbec et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2005/0228398 A1 | 10/2005 | Rathbun et al. |
| 2006/0122701 A1 | 6/2006 | Kiester |
| 2006/0129244 A1 | 6/2006 | Ensign |
| 2007/0218750 A1 | 9/2007 | Corrao et al. |
| 2007/0233150 A1 | 10/2007 | Blain et al. |
| 2007/0270859 A1 | 11/2007 | Companioni et al. |
| 2008/0132959 A1 | 6/2008 | Mikkonen et al. |
| 2008/0140207 A1* | 6/2008 | Olmos ............... A61F 2/4455 623/17.11 |
| 2009/0024158 A1 | 1/2009 | Viker |
| 2009/0292361 A1 | 11/2009 | Lopez |
| 2010/0076440 A1 | 3/2010 | Pamichev et al. |
| 2010/0082109 A1 | 4/2010 | Greenhalgh et al. |
| 2010/0152853 A1 | 6/2010 | Kirschman |
| 2010/0191336 A1 | 7/2010 | Greenhalgh |
| 2010/0211176 A1 | 8/2010 | Greenhalgh |
| 2010/0286777 A1 | 11/2010 | Errico et al. |
| 2011/0118843 A1 | 5/2011 | Mathieu et al. |
| 2011/0130838 A1 | 6/2011 | Morgenstern Lopez |
| 2011/0153020 A1 | 6/2011 | Abdelgany et al. |
| 2011/0218572 A1 | 9/2011 | Lechmann et al. |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215316 A1 | 8/2012 | Mohr et al. |
| 2013/0190876 A1 | 7/2013 | Drochner et al. |
| 2013/0211526 A1* | 8/2013 | Alheidt ............... A61F 2/4611 623/17.16 |
| 2013/0226191 A1 | 8/2013 | Thoren et al. |
| 2013/0231747 A1 | 9/2013 | Olmos et al. |
| 2013/0304136 A1 | 11/2013 | Gourlaouen-Preissler et al. |
| 2013/0317312 A1 | 11/2013 | Eastlack et al. |
| 2014/0107790 A1 | 4/2014 | Combrowski |
| 2014/0114321 A1 | 4/2014 | Davenport et al. |
| 2014/0114420 A1 | 4/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0249631 A1 | 9/2014 | Weiman |
| 2014/0277500 A1 | 9/2014 | Logan et al. |
| 2014/0303674 A1 | 10/2014 | Sasing |
| 2014/0364855 A1 | 12/2014 | Stoll et al. |
| 2015/0223945 A1 | 8/2015 | Weiman et al. |
| 2015/0230931 A1 | 8/2015 | Greenhalgh |
| 2015/0238236 A1 | 8/2015 | Sasing |
| 2016/0008924 A1 | 1/2016 | Canourgues et al. |
| 2016/0022434 A1 | 1/2016 | Robinson |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0095718 A1 | 4/2016 | Burkhardt et al. |
| 2016/0199073 A1 | 7/2016 | Nino et al. |
| 2016/0242930 A1 | 8/2016 | Duffield et al. |
| 2016/0256291 A1 | 9/2016 | Miller |
| 2016/0278830 A1 | 9/2016 | Arrington |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0224504 A1* | 8/2017 | Butler ............... A61F 2/447 623/17.16 |
| 2017/0231675 A1 | 8/2017 | Combrowski |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0367842 A1* | 12/2017 | Predick ............... A61F 2/4455 623/17.16 |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0000606 A1* | 1/2018 | Hessler ............... A61F 2/447 623/17.16 |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0104066 A1 | 4/2018 | Bae et al. |
| 2018/0116891 A1 | 5/2018 | Beale et al. |
| 2018/0193160 A1* | 7/2018 | Hsu ............... A61F 2/447 623/17.16 |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |

(56) References Cited

U.S. PATENT DOCUMENTS

| | | |
|---|---|---|
| 2018/0256362 A1 | 9/2018 | Slivka et al. |
| 2018/0263784 A1 | 9/2018 | Bechtel et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1* | 11/2018 | Engstrom ............... A61F 2/442 623/17.16 |
| 2018/0318102 A1 | 11/2018 | Seifert et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133779 A1 | 5/2019 | McLaughlin et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0247098 A1 | 8/2019 | Brumfield et al. |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262009 A1 | 8/2019 | Cheng |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328539 A1 | 10/2019 | Suh et al. |
| 2019/0328540 A1 | 10/2019 | Seifert et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0380840 A1 | 12/2019 | Tyber et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0069316 A1 | 3/2020 | DeSoutter et al. |
| 2020/0078190 A1 | 3/2020 | Rogers et al. |
| 2020/0093526 A1 | 3/2020 | Daly et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0179120 A1 | 6/2020 | Bielenstein et al. |
| 2020/0205993 A1 | 7/2020 | Davenport et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0281741 A1 | 9/2020 | Grotz |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |
| 2020/0397593 A1 | 12/2020 | Davenport et al. |
| 2020/0405497 A1 | 12/2020 | Olmos et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0007860 A1 | 1/2021 | Glerum et al. |
| 2021/0015626 A1 | 1/2021 | Suddaby |
| 2021/0030555 A1 | 2/2021 | Weiman et al. |
| 2021/0030561 A1 | 2/2021 | Gleason |
| 2021/0045891 A1 | 2/2021 | Rogers et al. |
| 2021/0045892 A1 | 2/2021 | Rogers et al. |
| 2021/0052395 A1 | 2/2021 | Iott et al. |
| 2021/0068959 A1 | 3/2021 | McLuen et al. |
| 2021/0068974 A1 | 3/2021 | Cowan et al. |
| 2021/0068982 A1 | 3/2021 | Carnes et al. |
| 2021/0077271 A1 | 3/2021 | Sharabani |
| 2021/0077272 A1 | 3/2021 | Eisen et al. |
| 2021/0085479 A1 | 3/2021 | Weiman et al. |
| 2021/0093462 A1 | 4/2021 | Lucasiewicz et al. |
| 2021/0106434 A1 | 4/2021 | Alheidt et al. |
| 2021/0113349 A1 | 4/2021 | Weiman et al. |
| 2021/0121299 A1 | 4/2021 | Hyder |
| 2021/0121300 A1 | 4/2021 | Weiman et al. |
| 2021/0137697 A1 | 5/2021 | Weiman |
| 2021/0137699 A1 | 5/2021 | Jang et al. |
| 2021/0137701 A1 | 5/2021 | Miller et al. |
| 2021/0154811 A1 | 5/2021 | Spreiter et al. |
| 2021/0161678 A1 | 6/2021 | Dewey et al. |
| 2021/0177618 A1 | 6/2021 | Branch et al. |
| 2021/0186706 A1 | 6/2021 | Spitler et al. |
| 2021/0186709 A1 | 6/2021 | Weiman et al. |
| 2021/0196470 A1 | 7/2021 | Shoshtaev |
| 2021/0205092 A1 | 7/2021 | Glerum et al. |
| 2021/0205094 A1 | 7/2021 | Weiman et al. |
| 2021/0220145 A1 | 7/2021 | Stein |
| 2021/0220147 A1 | 7/2021 | Berry |
| 2021/0236298 A1 | 8/2021 | Weiman et al. |
| 2021/0251770 A1 | 8/2021 | Purcell et al. |
| 2021/0251776 A1 | 8/2021 | Daffinson et al. |
| 2021/0259848 A1 | 8/2021 | Kang et al. |
| 2021/0259849 A1 | 8/2021 | Robinson et al. |

(56) References Cited

U.S. PATENT DOCUMENTS

| | | |
|---|---|---|
| 2021/0259850 A1 | 8/2021 | Eisen et al. |
| 2021/0267767 A1 | 9/2021 | Stein |
| 2021/0275317 A1 | 9/2021 | Spetzger |
| 2021/0275318 A1 | 9/2021 | Reimels |
| 2021/0275319 A1 | 9/2021 | Reimels |
| 2021/0275321 A1 | 9/2021 | Seifert et al. |
| 2021/0282938 A1 | 9/2021 | Nichols et al. |
| 2021/0298915 A1 | 9/2021 | Faulhaber |
| 2021/0298916 A1 | 9/2021 | Melkent et al. |
| 2021/0307920 A1 | 10/2021 | Walker et al. |
| 2021/0315705 A1 | 10/2021 | Altarac et al. |
| 2021/0322179 A1 | 10/2021 | Miller et al. |
| 2021/0322181 A1 | 10/2021 | Predick |
| 2021/0322182 A1 | 10/2021 | Faulhaber |
| 2021/0330472 A1 | 10/2021 | Shoshtaev |
| 2021/0346174 A1 | 11/2021 | Flint et al. |
| 2022/0015924 A1 | 1/2022 | Freedman et al. |
| 2022/0047312 A1 | 2/2022 | Seykora et al. |

FOREIGN PATENT DOCUMENTS

| | | |
|---|---|---|
| EP | 0 767 636 A1 | 4/1997 |
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| EP | 2954860 A2 | 12/2015 |
| EP | 3031424 A1 | 6/2016 |
| EP | 3 069 694 A1 | 9/2016 |
| EP | 3213720 A1 | 9/2017 |
| FR | 2781998 A1 | 2/2000 |
| FR | 3082115 A1 | 12/2019 |
| GB | 2 377 387 A | 1/2003 |
| KR | 102192022 B1 | 12/2020 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |
| WO | 2006116850 A1 | 11/2006 |
| WO | 2012139022 A2 | 10/2012 |
| WO | 2014/133755 A1 | 9/2014 |
| WO | 2015063721 A1 | 5/2015 |
| WO | 2015198335 A1 | 12/2015 |
| WO | 2016057940 A1 | 4/2016 |
| WO | 2017/168208 A1 | 10/2017 |
| WO | 2018049227 A1 | 3/2018 |
| WO | 2021055323 A1 | 3/2021 |

OTHER PUBLICATIONS

International Search Report and Written Opinion for Application No. PCT/US2019/019060, dated Jun. 5, 2019.
International Search Report and Written Opinion, PCT/IB2020/000942, dated Aug. 10, 2021.
International Search Report and Written Opinion, PCT/IB2020/000932, dated Jul. 29, 2021.
International Search Report and Written Opinion in Application No. PCT/US2022/016809 dated Jul. 27, 2022.
International Search Report and Written Opinion in Application No. PCT/US2022/027695 dated Jul. 27, 2022.
International Search Report and Written Opinion in Application No. PCT/US2022/027200 dated Aug. 19, 2022.
International Search Report and Written Opinion in Application No. PCT/US2022/030094 dated Sep. 16, 2022.

* cited by examiner

DUAL WEDGE EXPANDABLE IMPLANT, SYSTEM AND METHOD OF USE

CROSS REFERENCE TO RELATED APPLICATIONS

This application is a continuation in part of U.S. patent application Ser. No. 17/123,889, titled EXPANDABLE INTER-BODY DEVICE, SYSTEM, AND METHOD, filed Dec. 16, 2020 which claims priority to and incorporates by reference co-related international patent applications, PCT/IB2020/000942, titled Expandable Inter-Body Device, System, and Method, filed Nov. 5, 2020; and PCT/IB2020/000953, titled Expandable Inter-Body Device, System, and Method, filed Nov. 5, 2020. The contents of each are hereby incorporated in their entireties.

FIELD

The present disclosure generally relates to medical devices for the treatment of musculoskeletal disorders, and more particularly to a surgical device that includes an expandable spinal implant, systems for implanting and manipulating the expandable spinal implant, and a method for treating a human spine. In some embodiments, disclosed implants may be used in an anterior cervical discectomy and fusion (ACDF) procedure although other uses in other areas of the spine or for other orthopedic applications are also contemplated.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective; however, they may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody devices may be introduced to a space between adjacent vertebral bodies (the interbody space) to properly space the vertebral bodies and provide a receptacle for bone growth promoting materials (BGM), e.g., bone graft and/or synthetic materials.

Mechanically operated interbody implants may be used to align and/or realign a patient's spine during a medical procedure. Conventional implants designed for the Thoracic and Lumbar region of the spine often include top and bottom endplates and a mechanical means to separate the top and bottom endplates. The mechanical mechanisms to separate the top and bottom endplates are often cumbersome and require a large footprint that is often unsuitable for ACDF type surgeries of the cervical portion of the spine.

SUMMARY

The techniques of this disclosure generally relate, for example, to highly adjustable interbody devices that are expandable to selectively increase and decrease a spacing distance between superior and inferior endplates of the interbody device at either or both of a proximal end and/or a distal end of the implant.

In one aspect, an expandable implant movable between a contracted position and an expanded position, is disclosed. The implant may include, an expandable body extending from a proximal end to a distal end in a proximal-to-distal direction, extending from a first lateral side to a second lateral side in a widthwise direction, and extending from a superior end to an inferior end in a vertical direction, for example. In various embodiments, the expandable body may be defined by a superior endplate and an inferior endplate opposite the superior endplate, for example In various embodiments, the superior endplate may include a first outside surface and a first inside surface opposite the first outside surface, the first inside surface may include first proximal ramps and first distal ramps disposed opposite the first proximal ramps, for example In various embodiments, the inferior endplate may include a second outside surface and a second inside surface opposite the second outside surface, the second inside surface may include second proximal ramps and second distal ramps disposed opposite the second proximal ramps, for example. In various embodiments, a support block may be coupled to the superior endplate and the inferior endplate, the support block may have a proximal screw guide and a distal screw guide opposite the proximal screw guide, for example. In various embodiments, a proximal set screw rotatably supported by the proximal screw guide and a distal set screw rotatably supported by the distal screw guide may be provided, for example. In various embodiments, a proximal wedge may include first superior ramped surfaces and first inferior ramped surfaces, the proximal wedge may be coupled to the proximal set screw; and a distal wedge may include second superior ramped surfaces and second inferior ramped surfaces, the distal wedge may be coupled to the distal set screw, for example. In various embodiments, in a contracted position the proximal wedge and the distal wedge are disposed in a medial position of the body, for example. Additionally, in some embodiments, in a first expanded position a spacing between the superior and inferior endplates at the proximal side is greater than a spacing between the superior and inferior endplates at the proximal side in the contracted position, in the first expanded position the proximal wedge may contact the first superior ramped surfaces and the first inferior ramped surfaces and is disposed proximate the proximal side, for example. Additionally, in some embodiments, in a second expanded position a spacing between the superior and inferior endplates at the distal side is greater than a spacing between the superior and inferior endplates at the distal side in the contracted position, in the second expanded position the distal wedge may contact the first and second proximal ramps and is disposed proximate the proximal side with respect to the medial position, for example.

In another aspect, a spinal implant system is disclosed. The spinal implant system may include an expandable implant movable between a contracted position and an expanded position. The implant may include, an expandable body extending from a proximal end to a distal end in a proximal-to-distal direction, extending from a first lateral side to a second lateral side in a widthwise direction, and extending from a superior end to an inferior end in a vertical direction, for example. In various embodiments, the expandable body may be defined by a superior endplate and an inferior endplate opposite the superior endplate, for example In various embodiments, the superior endplate may include a first outside surface and a first inside surface opposite the first outside surface, the first inside surface may include first proximal ramps and first distal ramps disposed opposite the first proximal ramps, for example. In various embodiments, the inferior endplate may include a second outside surface and a second inside surface opposite the second outside surface, the second inside surface may include second proximal ramps and second distal ramps disposed opposite the second proximal ramps, for example In various embodiments, a support block may be coupled to the superior endplate and the inferior endplate, the support block may have a proximal screw guide and a distal screw guide opposite the proximal screw guide, for example. In various embodiments, a proximal set screw rotatably supported by the proximal screw guide and a distal set screw rotatably supported by the distal screw guide may be provided, for example In various embodiments, a proximal wedge may include first superior ramped surfaces and first inferior ramped surfaces, the proximal wedge may be coupled to the proximal set screw; and a distal wedge may include second superior ramped surfaces and second inferior ramped surfaces, the distal wedge may be coupled to the distal set screw, for example. In various embodiments, in a contracted position the proximal wedge and the distal wedge are disposed in a medial position of the body, for example. Additionally, in some embodiments, in a first expanded position a spacing between the superior and inferior endplates at the proximal side is greater than a spacing between the superior and inferior endplates at the proximal side in the contracted position, in the first expanded position the proximal wedge may contact the first superior ramped surfaces and the first inferior ramped surfaces and is disposed proximate the proximal side, for example Additionally, in some embodiments, in a second expanded position a spacing between the superior and inferior endplates at the distal side is greater than a spacing between the superior and inferior endplates at the distal side in the contracted position, in the second expanded position the distal wedge may contact the first and second proximal ramps and is disposed proximate the proximal side with respect to the medial position, for example. Additionally, in various embodiments, the support block may further include a plurality of engagement prongs extending towards the proximal end in the proximal-to-distal direction, for example. Additionally, the system may include an insertion tool extending in a longitudinal direction from a proximal end to a distal end thereof, and the insertion tool may include a plurality of engagement arms that may have a size and shape corresponding to the plurality of engagement prongs, for example In another aspect, an expandable and contractable spinal implant is disclosed. The implant may include an expandable body extending from a proximal end to a distal end in a proximal-to-distal direction, extending from a first lateral side to a second lateral side in a widthwise direction, and extending from a superior end to an inferior end in a vertical direction, the expandable body may be defined by a superior endplate and an inferior endplate opposite the superior endplate, for example. In various embodiments, the superior endplate may include a first outside surface and a first inside surface opposite the first outside surface, the first inside surface may include first proximal ramps and first distal ramps disposed opposite the first proximal ramps, for example. In various embodiments, the inferior endplate may include a second outside surface and a second inside surface opposite the second outside surface, the second inside surface may include second proximal ramps and second distal ramps disposed opposite the second proximal ramps, for example. In various embodiments, a support block may be coupled to the superior endplate and the inferior endplate, the support block may have a proximal screw guide and a distal screw guide opposite the proximal screw guide, for example. Additionally, the proximal screw guide may define a first rotation axis and the distal screw guide may define a second rotation axis, the first and second rotation axes may extend in the proximal-to-distal direction, for example. In various embodiments, a proximal set screw rotatably supported by the proximal screw guide and a distal set screw rotatably supported by the distal screw guide may be provided. In various embodiments, a proximal wedge may be to the proximal set screw and may include first superior ramped surfaces and first inferior ramped surfaces, and a distal wedge may be coupled to the distal set screw and may include second superior ramped surfaces and second inferior ramped surfaces, for example. In various embodiments, the proximal wedge may be coupled to the proximal set screw and movable toward and away from the proximal end in the proximal-to-distal direction by rotation of the proximal set screw along the first rotation axis, the distal wedge may be coupled to the distal set screw and movable toward and away the distal end in the proximal-to-distal direction by rotation of the distal set screw along the second rotation axis, for example. Additionally, in various embodiments, the proximal wedge and distal wedge may be configured to simultaneously distract the superior and inferior endplates in a parallel manner upon simultaneous rotation of both the proximal set screw and distal set screw in a first direction and simultaneously contract the superior and inferior endplates in a parallel manner upon simultaneous rotation of both the proximal set screw and distal set screw in a second direction opposite the first direction, for example. In various embodiments, the proximal set screw may be configured to urge the proximal wedge towards the proximal end in the proximal-to-distal direction upon independent rotation of the proximal set screw in the first direction, thereby distracting the superior and inferior endplates at the proximal end, for example. In various embodiments, the distal set screw may be configured to urge the distal wedge towards the distal end in the proximal-to-distal direction upon independent rotation of the distal set screw in the first direction, thereby distracting the superior and inferior endplates at the distal end.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 34 is a reference drawing showing the human spine of which various disclosed implant embodiments may be installed in.

FIG. 35 is a reference drawing showing various planes and reference directions of which the various disclosed implant embodiments may move in or act in.

DETAILED DESCRIPTION

Figure 1A:
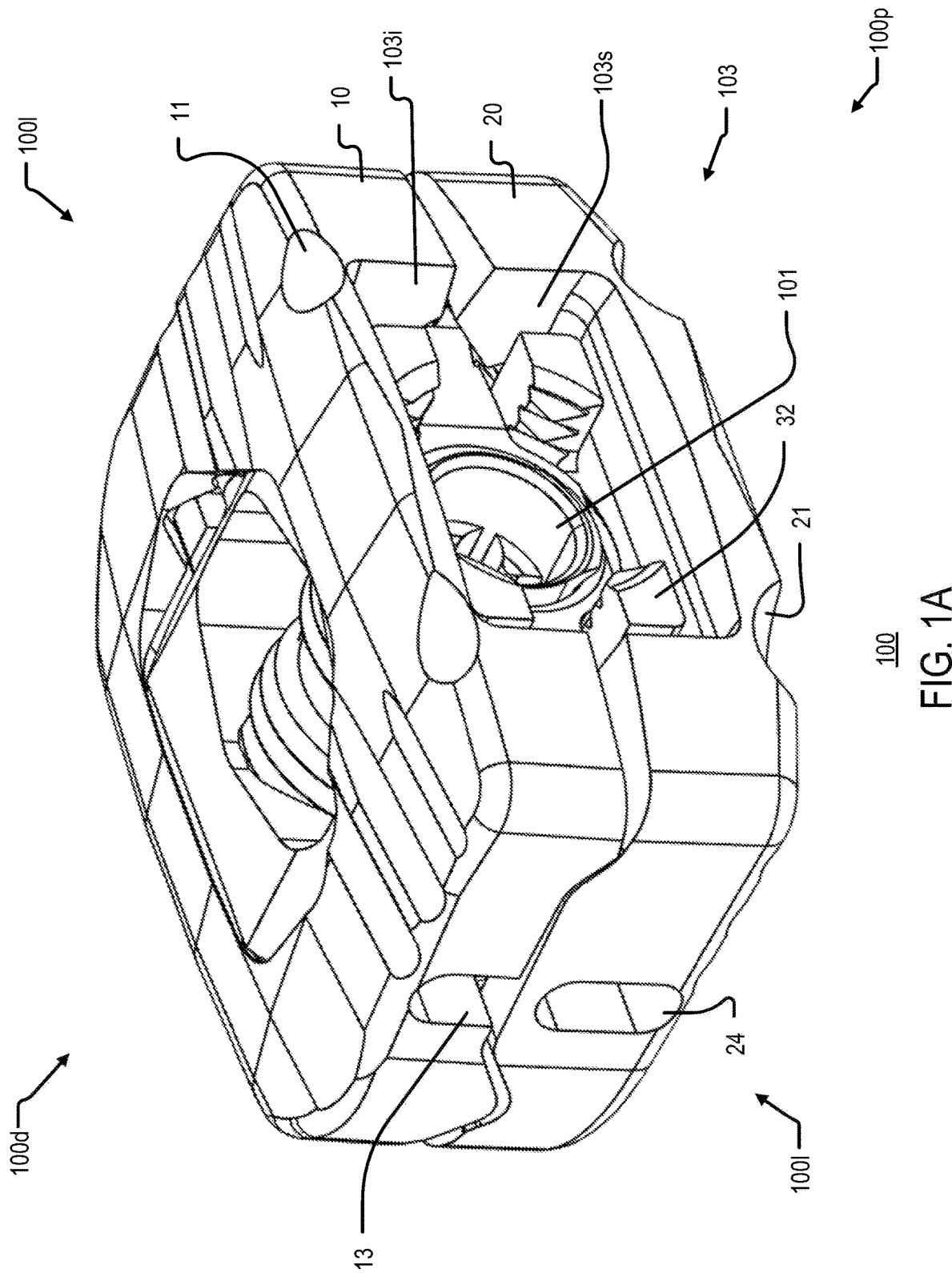
FIG. 1A is a front perspective view of an expandable implant.
Figure 1B:
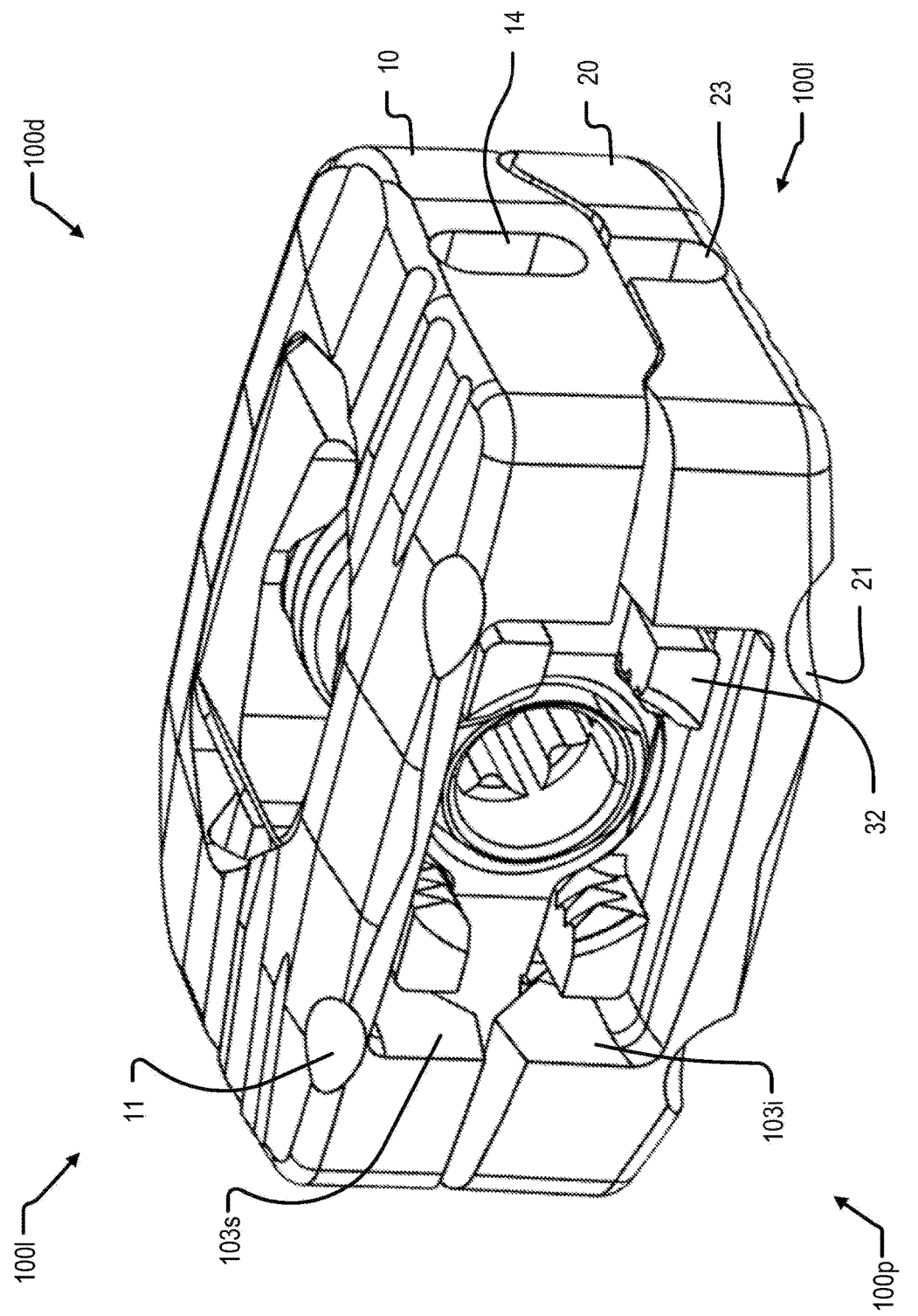
FIG. 1B is an alternate front perspective view of an expandable implant.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Figure 2:
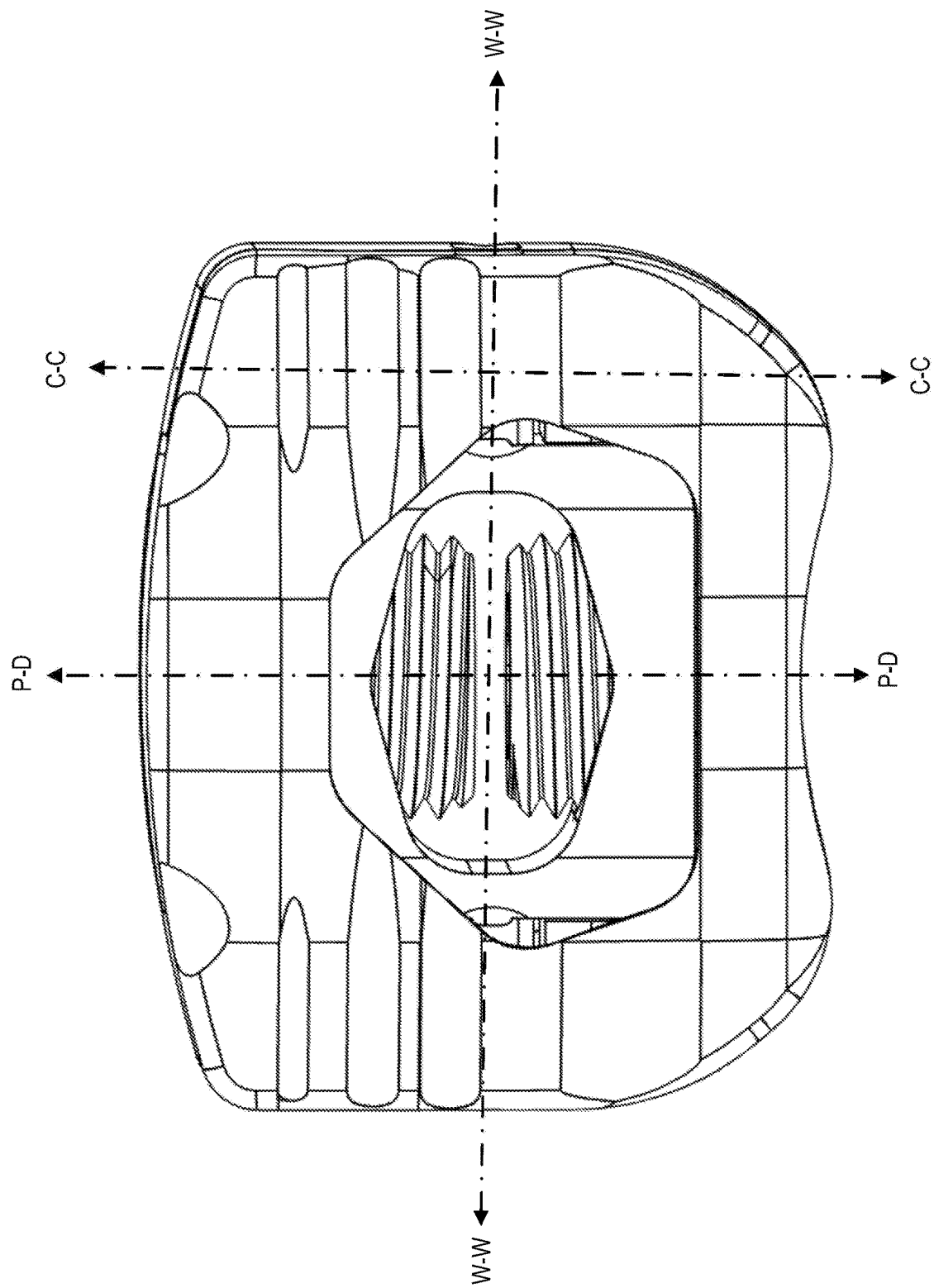
FIG. 2 is a top down view of an expandable implant.
Figure 3:
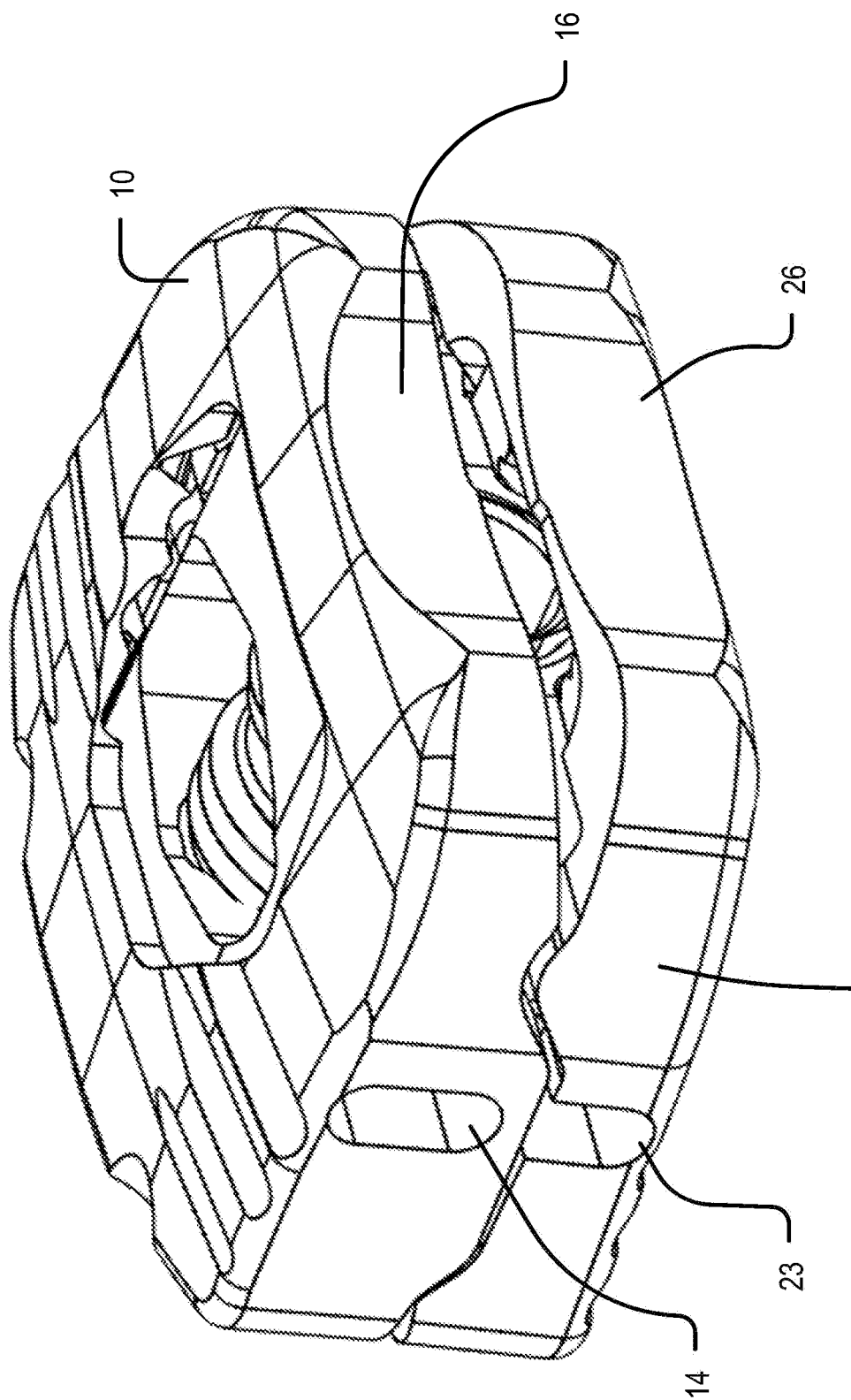
FIG. 3 is a front perspective view of an expandable implant.
Figure 4:
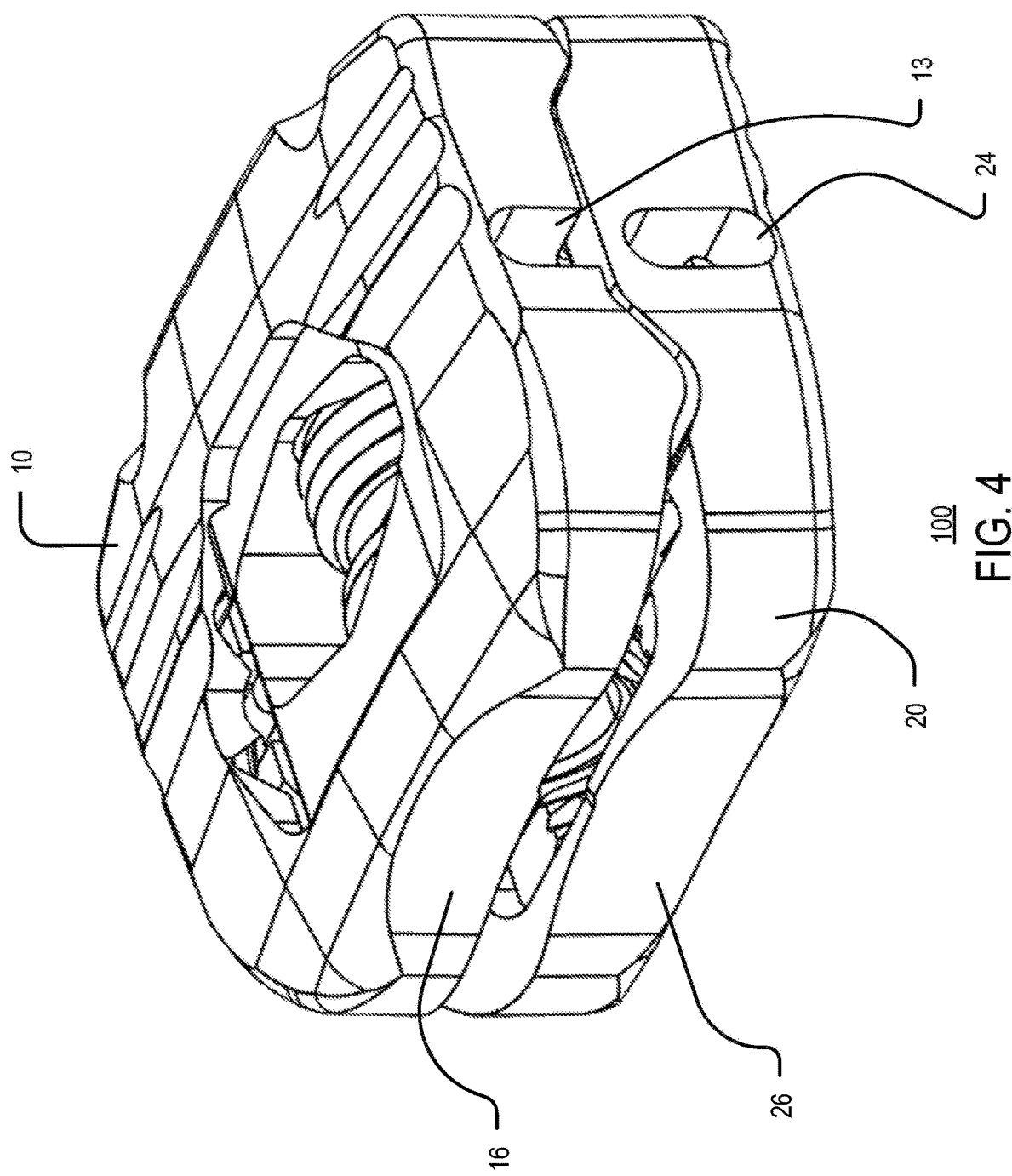
FIG. 4 is an alternate front perspective view of an expandable implant.

Referring generally to FIGS. 1-4 various views of an expandable implant are illustrated. For example, FIGS. 1A-1B and 3-4 are various perspective views of an expandable implant 100 and FIG. 2 is a top down view of an expandable implant showing various axes and points of reference. As illustrated, expandable implant 100 may include a proximal end 100p, a distal end 100d, and first and second lateral sides 1001. The proximal end 100p may include an adjustment aperture 101 and an engagement cutout 103 for use with various surgical tools disclosed in FIGS. 21-33. As shown in FIG. 2, implant 100 may extend in a proximal-to-distal direction from the proximal end 100p to the distal end 100d though axis P-D through the center of the implant 100, for example Implant 100 may extend in a widthwise direction from the first lateral side 1001 to the second lateral side 1001 through a widthwise axis W-W through the center of the implant 100, for example Axis P-D may be perpendicular and/or substantially perpendicular to the widthwise axis B-B. Various example section cuts through cross section C-C are illustrated in FIGS. 17-20. In various embodiments, superior endplate 10 may include connection points 11 and inferior endplate 20 may include connection points 21. Connection points 11, 21 may be indentations along the proximal end of each of superior and inferior endplates 10, 20, for example. In various embodiments, connection points 11, 21 may be used to secure a bone screw plate (not illustrated) and the bone screw plate may include various apertures and fasteners for securing bone screws to a boney structure, such as a vertebrae. Superior endplate 10 may include a first slot 13 and a second slot 14 on opposite lateral ends thereof, for example Similarly, inferior endplate 20 may include a third slot 23 and a fourth slot 24 on opposite lateral ends thereof, for example. Slots 13, 14, 23, 24 may be used to constrain a support block 30 (see FIG. 5) within the interior of the superior and inferior endplates 10, 20. A distal side of superior endplate 10 may include a curved indentation 16 for accommodating the spinal canal. Similarly, inferior endplate 20 may include a curved indentation 26 for accommodating the spinal canal. The curved indentations may be curved inward towards a medial portion of implant (e.g., from a distal end 100d towards a proximal end 100p) and extend in the width wise direction W-W, for example.

Figure 5:
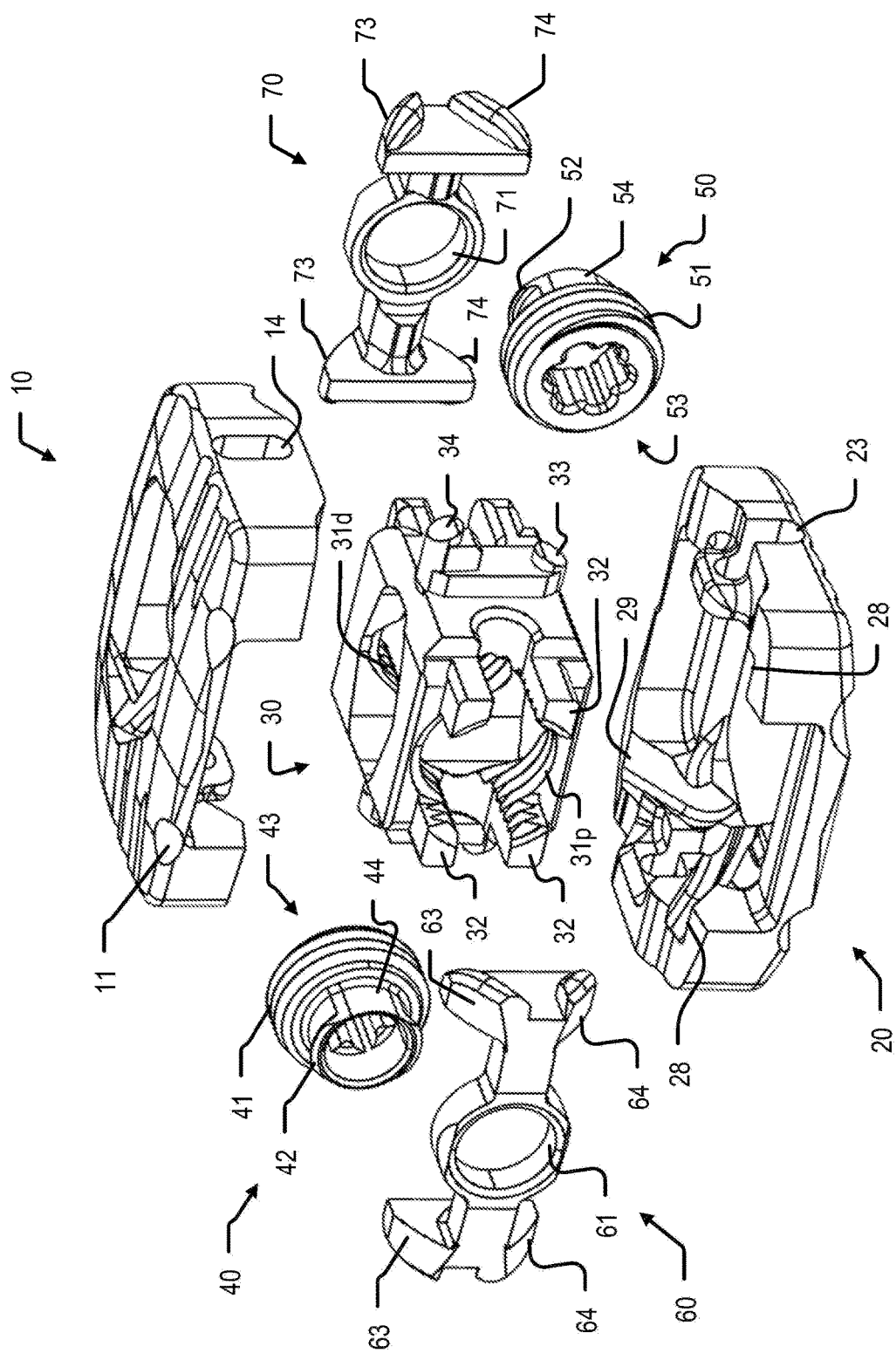
FIG. 5 is an exploded parts view of an expandable implant.
Figure 6:
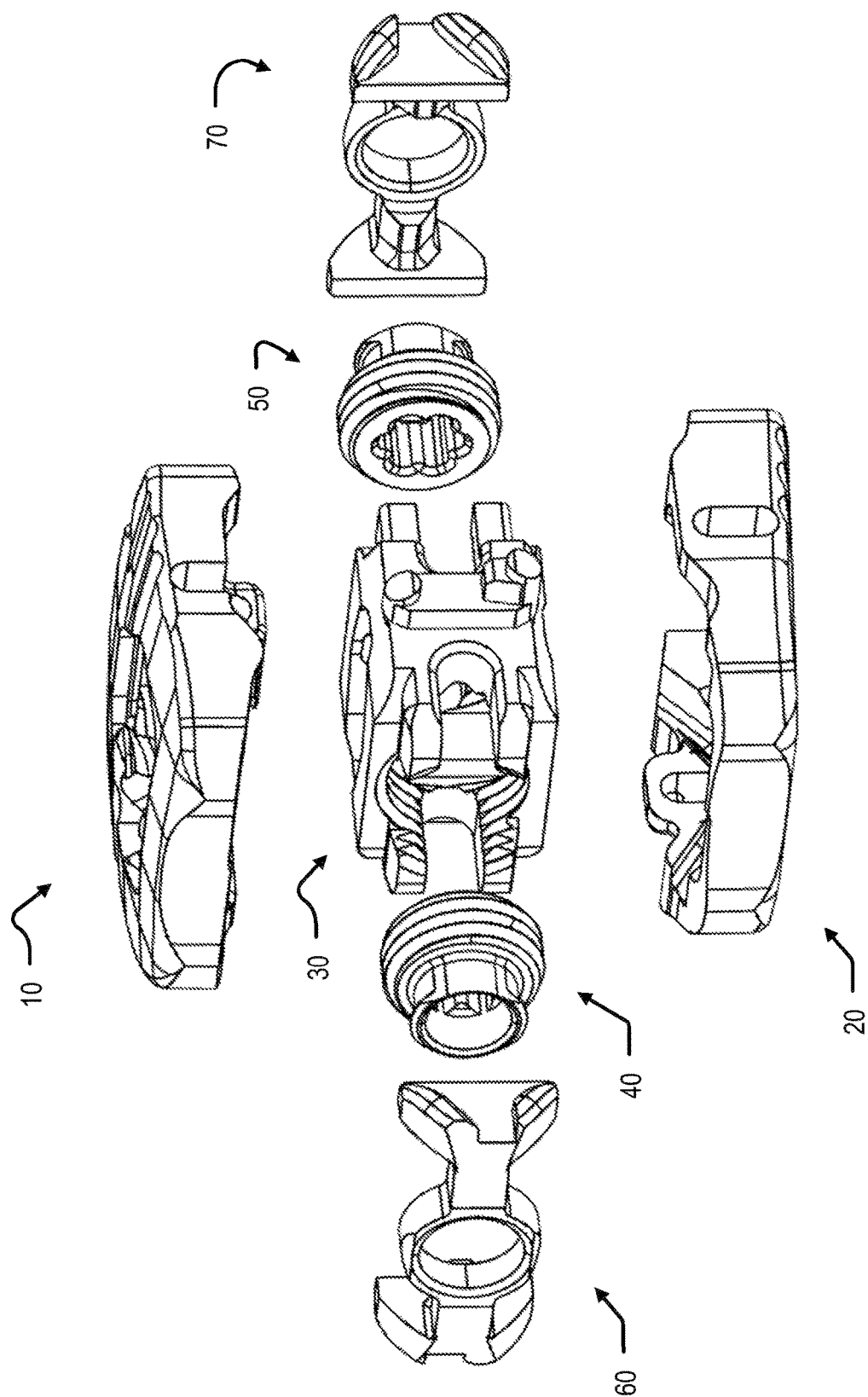
FIG. 6 is an alternate exploded parts view of an expandable implant.

FIGS. 5-6 are various exploded parts views of an expandable implant 100. The superior and inferior endplates 10, 20 may be movable with respect to one another in the vertical direction and also may be inclinable, e.g., capable of distraction and lordosis and even kyphotic adjustments. The superior endplate 10 and inferior endplate 20 may be operably engaged and/or coupled with one another by a support block 30, for example. Support block 30 may include a first post 34 and a second post 33 on each lateral side surface of support block 30. For example, first post 34 may be an elongate cylindrical post extending in the widthwise direction W-W from support block and second post 33 may be a relatively shorter elongate cylindrical post extending in the widthwise direction, for example. Additionally in some embodiments, post 34 and post 33 may have an inclined end cap having a planar end surface approximating the shape of an oval Similarly, the other lateral side of support block 30 may also include a first post 34 and a second post 33. In some embodiments, the posts 34, 33 on opposite lateral ends may be transposed. For example, on a first lateral end, post 34 may be above post 33 and on the other lateral end post 33 may be above post 34. This arrangement may facilitate the symmetrical transference of forces throughout implant 100, for example. Additionally, posts 34 may extend through slotted apertures 14, 24 of superior and inferior endplates 10, 20, for example. Similarly, posts 33 may extend through slotted apertures 13, 23 of superior and inferior endplates 10, 20, for example.

Support block 30 may include a plurality of engagement prongs 32 or post like structures extending towards proximal end 100p. In the example illustration, four engagement prongs 32 are symmetrically distributed at respective corners of a proximal end of support block 30. However, other embodiments may include more or less engagement prongs 32, for example, 1, 2, 3, 5, 6, etc. Engagement prongs 32 may be used to couple implant 100 to an inserter tool 200, as will be explained in further detail below. Support block 30 may include a proximal screw guide 31p and a distal screw guide 31d. The proximal and distal screw guides 31p, 31d may each be defined by a circular aperture having an internal circumferential surface including a thread pattern and define a rotation axis extending through a center of the thread pattern, respectively. In some embodiments, the thread patterns may be reversed and in other embodiments they may be the same. The proximal screw guide 31p may rotatably support a proximal set screw 40 and the distal screw guide 31d may rotatably support a distal set screw 50, for example The proximal set screw 40 may include a thread pattern 41 extending along a portion of the outside circumferential surface thereof and a drive engagement surface 43 extending along a portion of the inside circumferential surface thereof. A remaining portion of the outside circumferential surface thereof may be defined by a diameter that is less than a diameter of the portion of set screw 40 having thread pattern 41, for example. For example, a smooth circumferential surface 44 that is inset towards an axial centerline of set screw 40 and with respect to thread pattern 41. For example still, one end of set screw 40 may include a thread pattern 41 and the other end may include an inset circumferential surface 44 having at least one flange 42 on an end thereof. In some embodiments, an upper and lower flange 42 are provided, and in other embodiments the flange 42 extends all the way around the end of circumferential surface 44 as an annular ring. Similarly, the distal set screw 50 may include a thread pattern 51 extending along a portion of the outside circumferential surface thereof and a drive engagement surface 53 extending along a portion of the inside circumferential surface thereof. A remaining portion of the outside circumferential surface thereof may be defined by a diameter that is less than a diameter of the portion of set screw 50 having thread pattern 51, for example. For example, a smooth circumferential surface 54 that is inset towards an axial centerline of set screw 50 with respect to thread pattern 51. For example still, one end of set screw 50 may include a thread pattern 51 and the other end may include an inset circumferential surface 54 having at least one flange 52 extending from an end thereof. In some embodiments, an upper and lower flange 52 are provided, and in other embodiments the flange 52 extends all the way around the end of circumferential surface 54 as an annular ring.

Implant 100 may include a proximal wedge structure 60 and a distal wedge structure 70. Proximal wedge structure 60 may be operably coupled to proximal set screw 40 and distal wedge structure 70 may be operably coupled to distal set screw 50, for example. Proximal wedge 60 may include an aperture 61 having a size and shape corresponding to circumferential surface 44. For example, set screw 40 may be coupled to proximal wedge 60 by disposing the circumferential surface 44 within aperture 61 such that flanges 42 extend through aperture 61 and securely couple the proximal wedge 60 with proximal set screw 40 such that proximal set screw 40 may rotate within aperture 61. Additionally, flange 42 may permit axial translation of forces, for example by pushing and/or pulling. Proximal wedge 60 may further include a pair of superior ramped surfaces 63 and a pair of inferior ramped surfaces 64. Superior ramped surfaces 63 may be disposed on opposite lateral ends of proximal wedge 60 from one another and inferior ramped surface 64 may be disposed on opposite lateral ends of proximal wedge 60 from one another. Similarly, distal wedge structure 70 may include an aperture 71 having a size and shape corresponding to circumferential surface 54 of distal set screw 50. For example, set screw 50 may be coupled to distal wedge 70 by disposing the circumferential surface 54 within aperture 71 such that flanges 52 extend through aperture 71 and securely couple the distal wedge 70 with distal set screw 50 such that distal set screw 50 may rotate within aperture 71 and permit axial translation of forces. Distal wedge 70 may further include a pair of superior ramped surfaces 73 and a pair of inferior ramped surfaces 74. Superior ramped surfaces 73 may be disposed on opposite lateral ends of distal wedge 70 from one another and inferior ramped surfaces 74 may be disposed on opposite lateral ends of distal wedge 70 from one another.

Figure 7:
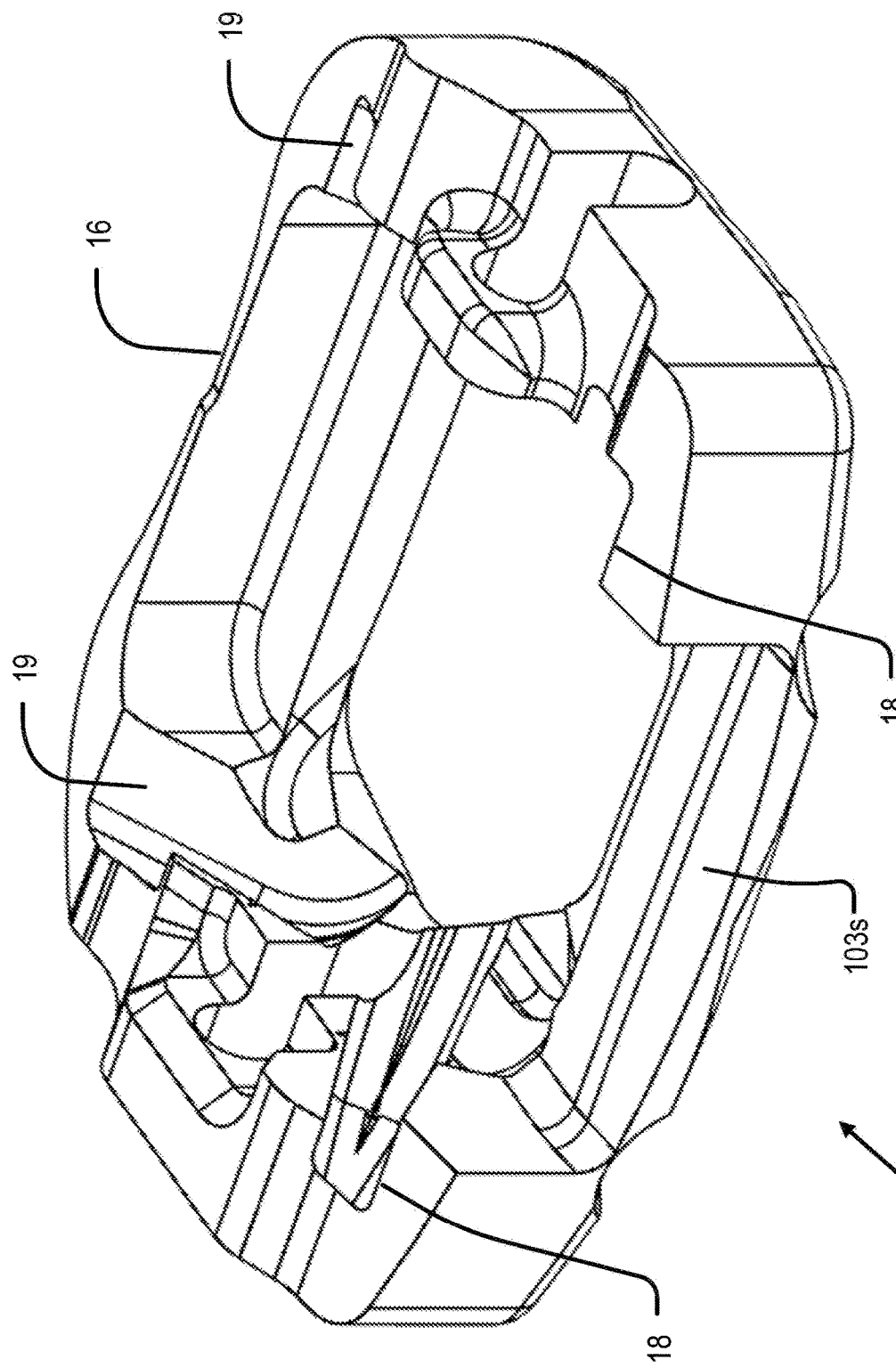
FIG. 7 is an interior view of a superior endplate.
Figure 8:
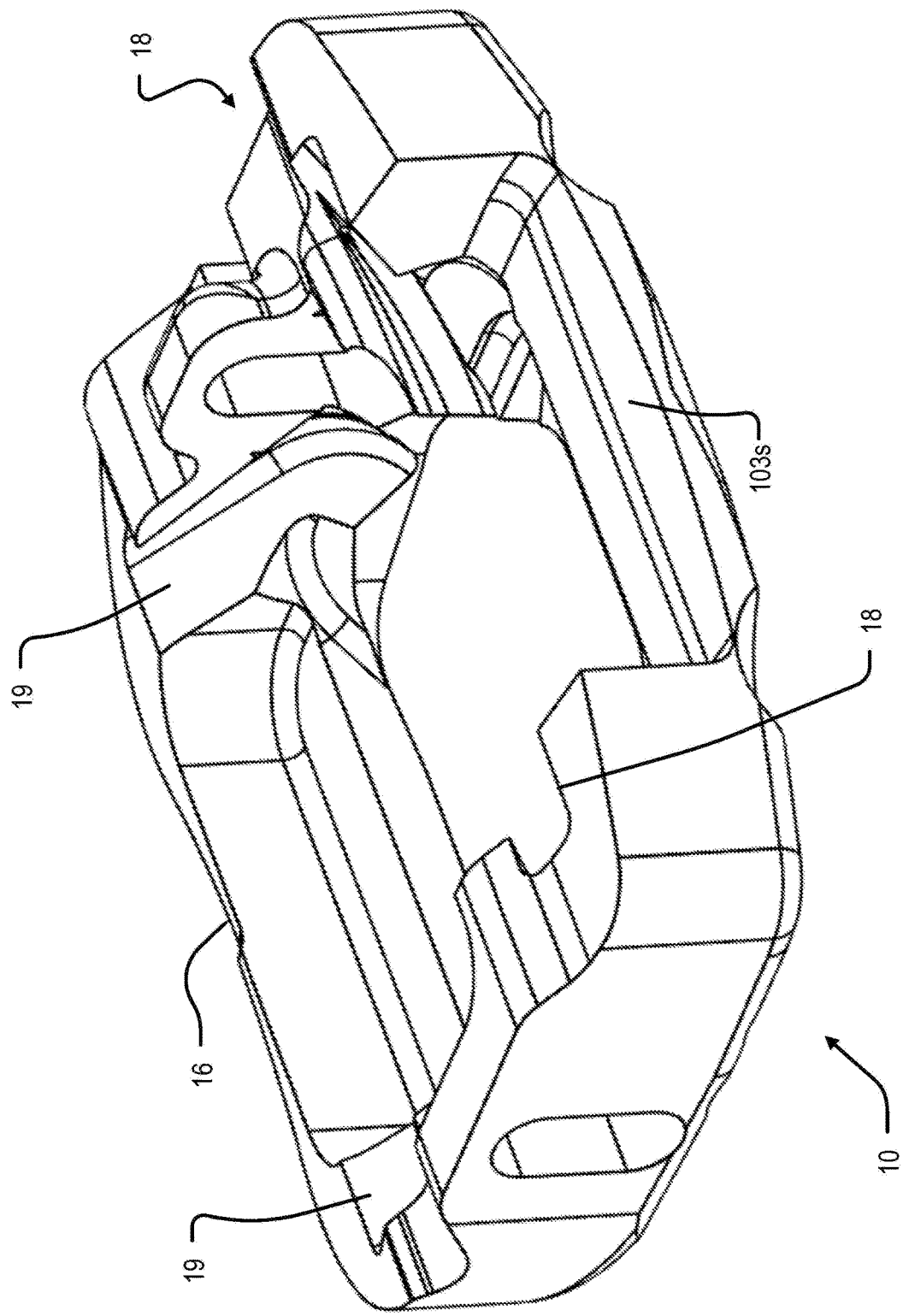
FIG. 8 is an alternate interview of a superior endplate.
Figure 9:
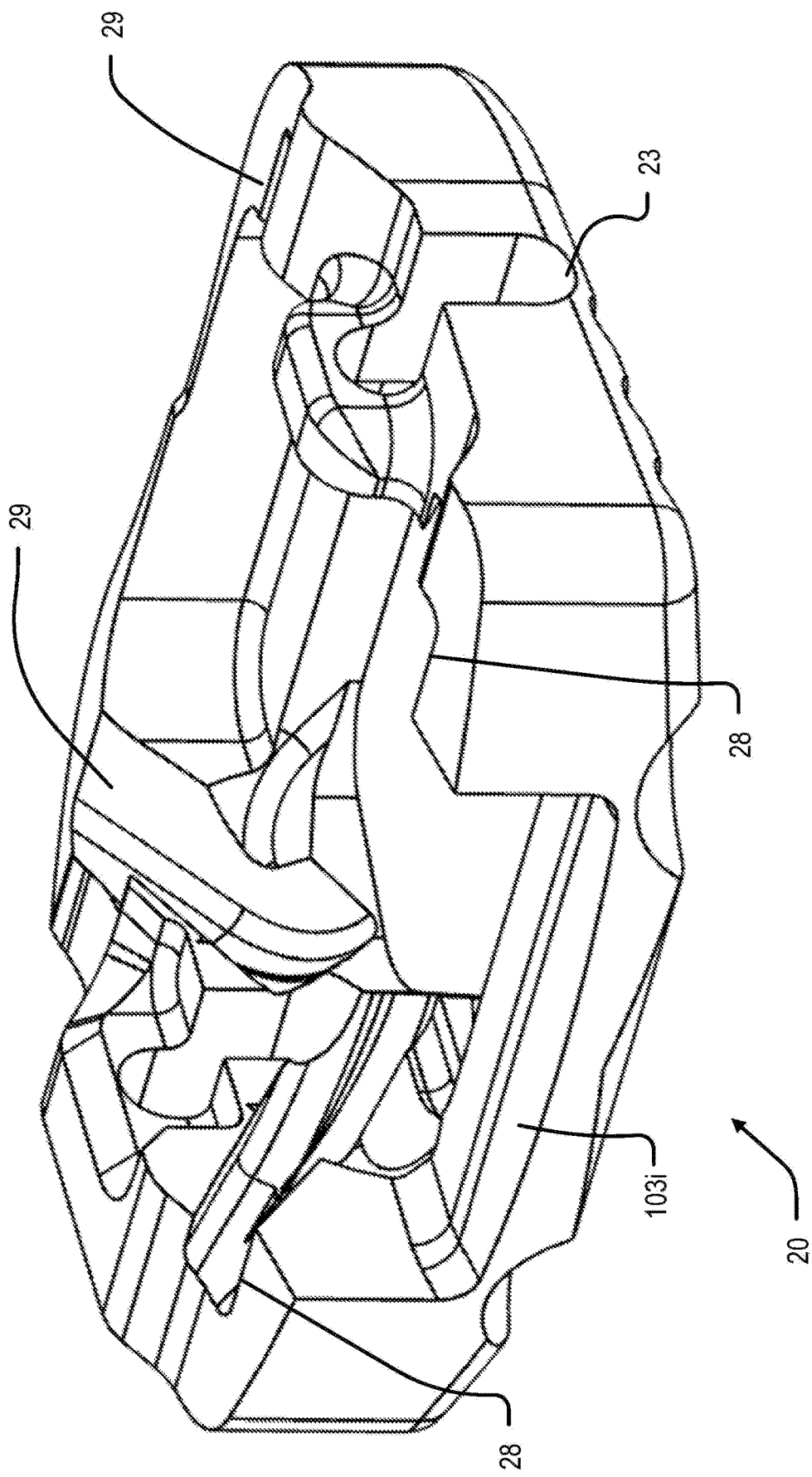
FIG. 9 is an interior view of an inferior endplate.
Figure 10:
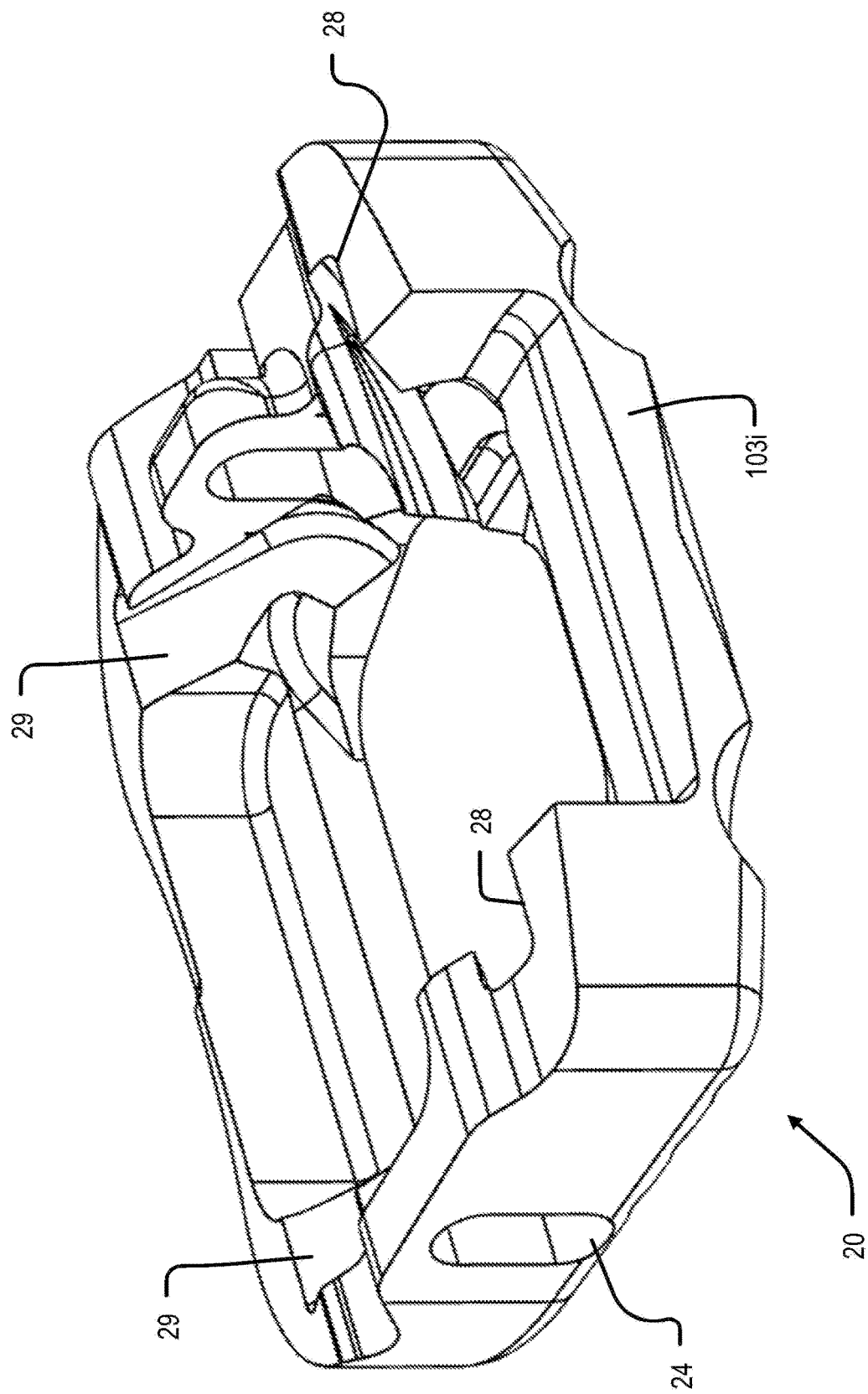
FIG. 10 is an alternate interview of a inferior endplate.

Referring generally to FIGS. 7-8, there are various interior views of an interior of a superior endplate 10 and referring generally to FIGS. 9-10, there are various views of an interior of an inferior endplate. The proximal wedge 60 and distal wedge 70 may act against various surfaces of superior and inferior endplates 10, 20 to expand, contract, and incline implant 100 in various positions. For example, superior endplate 10 may include a pair of proximal ramps 18 that are disposed proximate the proximal end of superior endplate 10 and are inclined from a medial position of superior endplate 10 towards the proximal end 100p of implant 100, for example. In the disclosed embodiment, a first proximal ramp 18 and a second proximal ramp 18 are disposed on opposite sides of superior engagement cutout 103s. Additionally, superior endplate 10 may include a pair of distal ramps 19 that are disposed proximate the distal end of superior endplate 10 and are inclined from a medial position of superior endplate 10 towards the distal end 100d of implant 100. In the disclosed embodiment, a first distal ramp 19 and a second distal ramp 19 are disposed on opposite sides of curved indentation 16, for example.

Similarly, inferior endplate 20 may include a pair of proximal ramps 28 that are disposed proximate the proximal end of inferior endplate 20 and are inclined from a medial position of inferior endplate 20 towards the proximal end 100p of implant 100, for example For example, inferior endplate 20 may include a pair of proximal ramps 28 that are disposed proximate the proximal end of inferior endplate 20 and are inclined from a medial position of inferior endplate 20 towards the proximal end 100p of implant 100, for example. In the disclosed embodiment, a first proximal ramp 28 and a second proximal ramp 28 are disposed on opposite sides of inferior engagement cutout 103i. Additionally, inferior endplate 20 may include a pair of distal ramps 29 that are disposed proximate the distal end of inferior endplate 20 and are inclined from a medial position of inferior endplate 20 towards the distal end 100d of implant 100. In the disclosed embodiment, a first distal ramp 29 and a second distal ramp 29 are disposed on opposite sides of curved indentation 26, for example. As will be explained in more detail below, superior ramped surfaces 63 of proximal wedge 60 may directly contact and act against proximal ramps 18 of superior endplate 10 and inferior ramped surfaces 64 of proximal wedge 60 may directly contact and act against proximal ramps 28 of inferior endplate 20. As will be explained in more detail below, superior ramped surfaces 73 of distal wedge 70 may directly contact and act against distal ramps 19 of superior endplate 10 and inferior ramped surfaces 74 of distal wedge 70 may directly contact and act against distal ramps 29 of inferior endplate 20.

Figure 11:
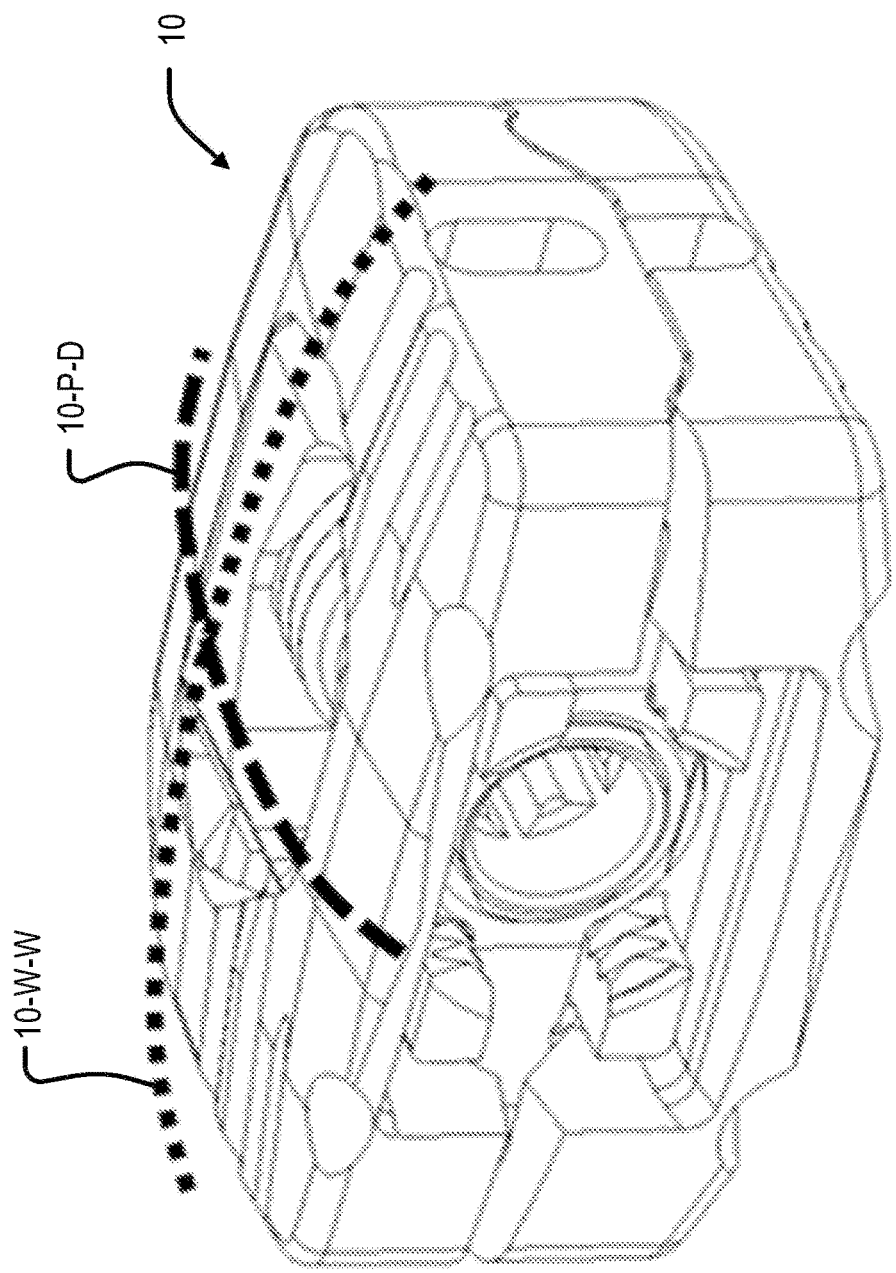
FIG. 11 is a front perspective view of a superior portion of expandable implant.
Figure 12:
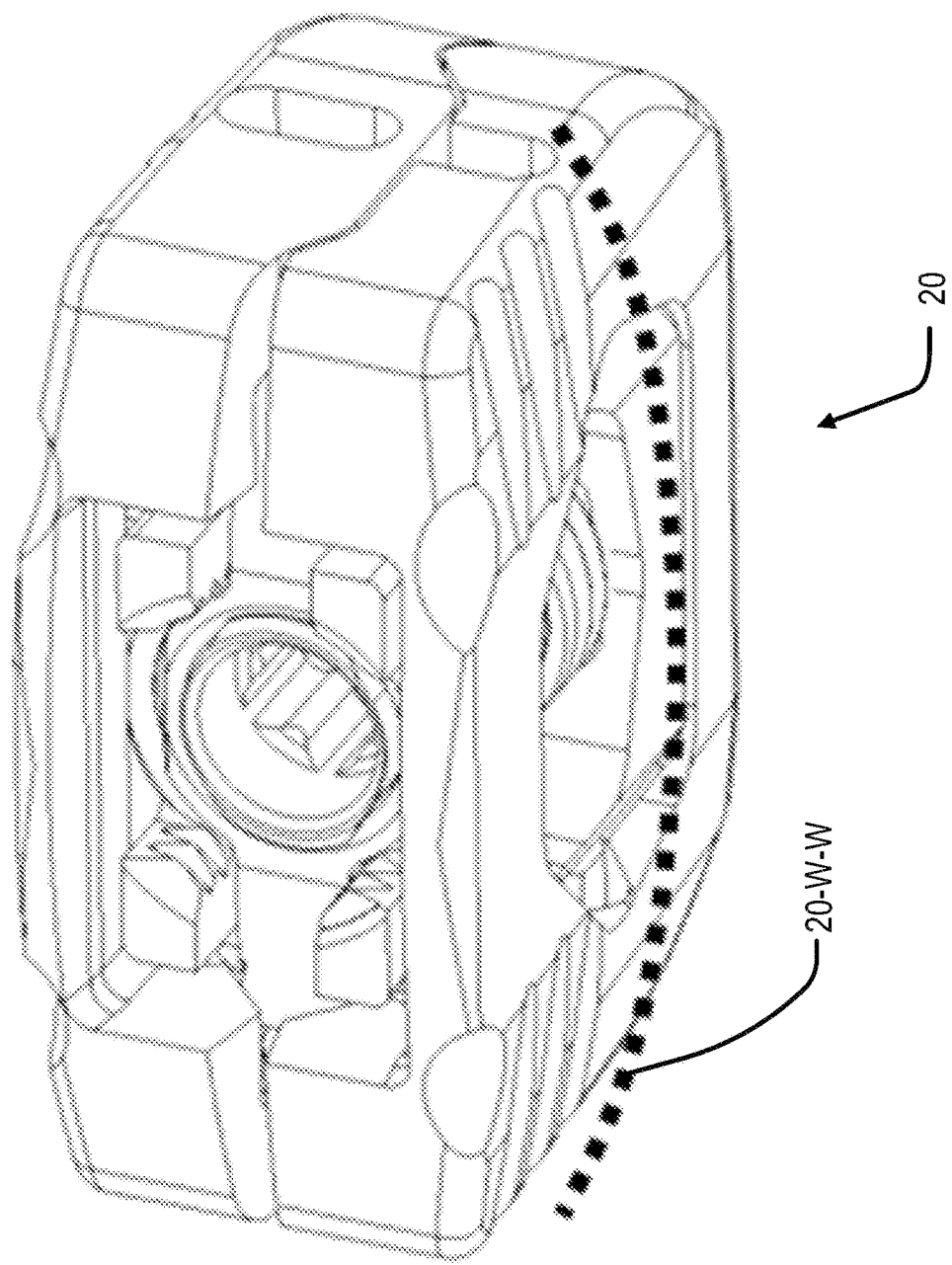
FIG. 12 is a front perspective view of an inferior portion of expandable implant.

Referring generally to FIGS. 11-16, there are various perspective views of an expandable implant 100 in a contracted position and in various expanded configurations. As shown in FIG. 11, superior endplate 10 is bi-concave. For example, superior endplate 10 is concave in the proximal-to-distal direction P-D along curved line 10-P-D and superior endplate 10 is concave in the widthwise direction W-W along curved line 10-W-W. This arrangement may be advantageous for mating with the concavity of a lower surface of a superior endplate of an adjacent vertebrae (not illustrated), for example. Other embodiments may have substantially planar upper surfaces and/or be concave in only one of the proximal-to-distal direction P-D and widthwise direction W-W. For example, inferior endplate 20 may be uni-convex. As shown in FIG. 12, the inferior endplate 20 is convex in at least one direction. For example, inferior endplate is convex in a widthwise direction W-W along curved line 20-W-W. This arrangement may be advantageous for mating with the concavity of an upper surface of an inferior endplate of an adjacent vertebrae (not illustrated). In some embodiments, the curvature of the superior endplate 10 and inferior endplate 20 may be lordotic relative to one another. In some embodiments, the curvature of the superior endplate 10 and inferior endplate 20 may have different amounts of lordosis relative to a central horizontal plane of support block 30, for example.

Figure 13:
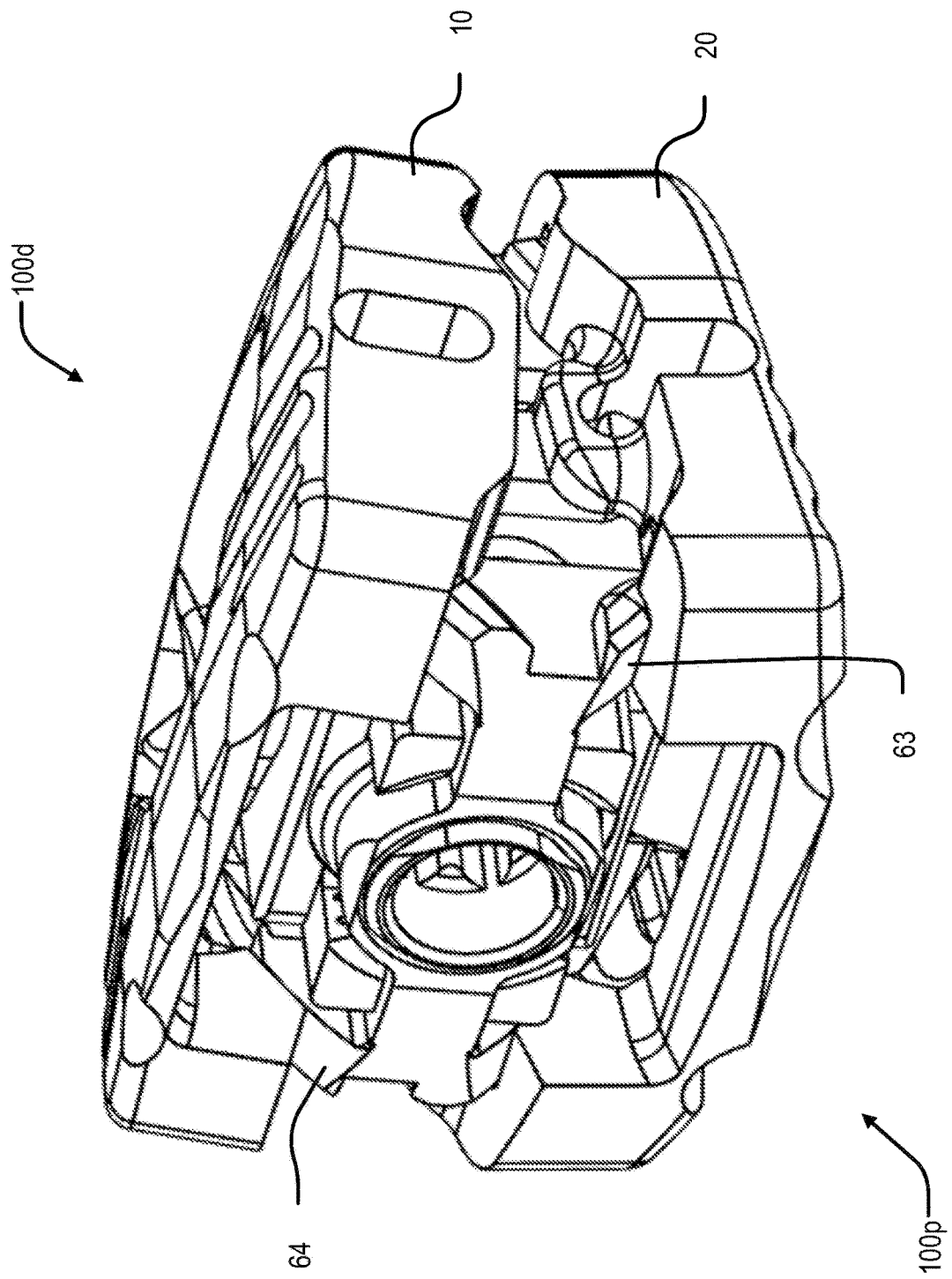
FIG. 13 is a front perspective view of an expandable implant in a first expanded configuration.
Figure 14:
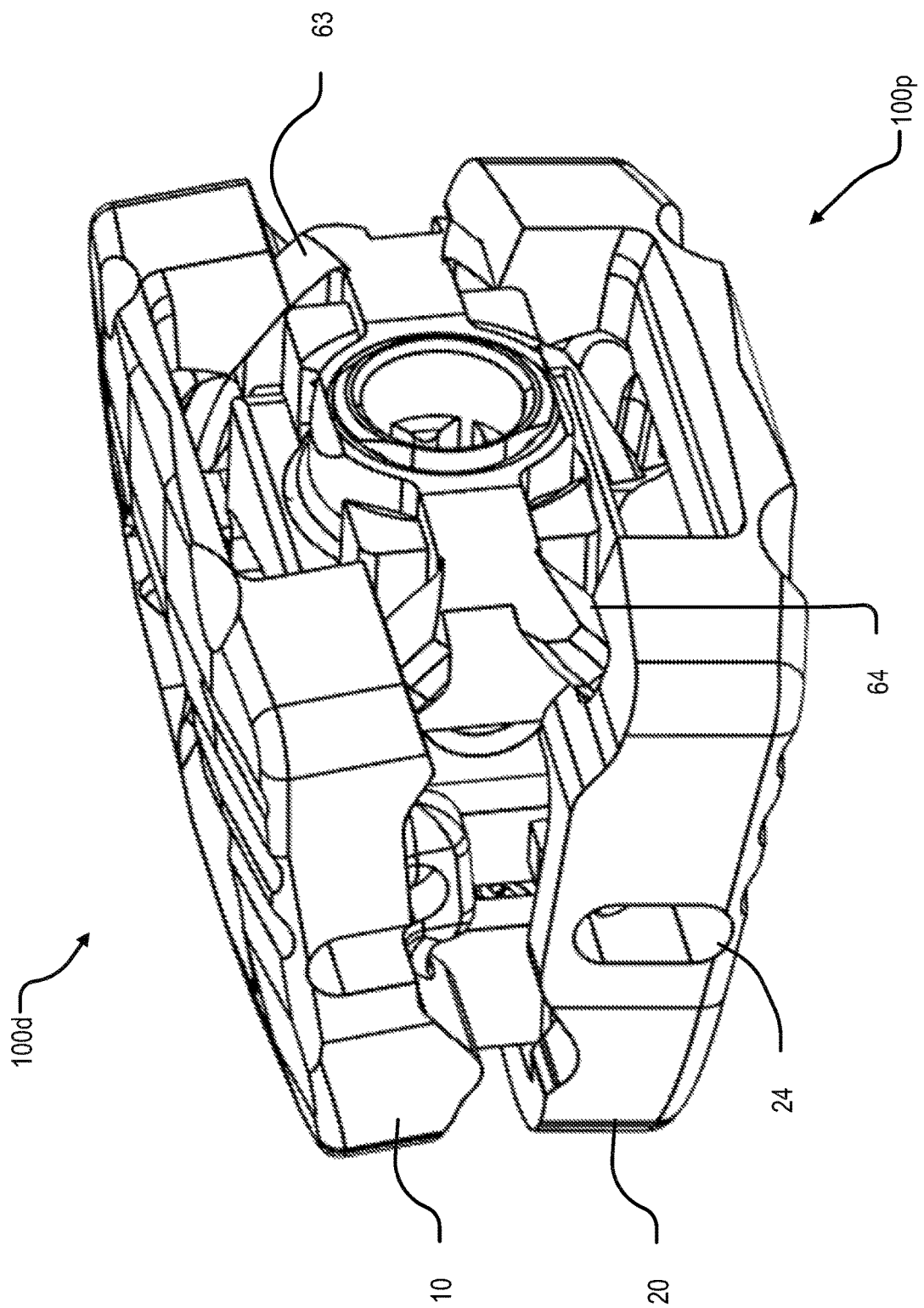
FIG. 14 is an alternate front perspective view of an expandable implant in a first expanded configuration.

FIG. 13 illustrates an example configuration of implant 100 in an expanded and inclined position, e.g., a partially distracted and lordosed position. In FIGS. 13-14, it is illustrated that the proximal wedge 60 has moved towards the proximal end 100p of implant 100 in the proximal-to-distal direction P-D, for example. Proximal wedge 60 may have moved towards the proximal end 100p from a medial position due to proximal set screw 40 being rotated within proximal screw guide 31p such that proximal set screw 40 is linearly translated towards proximal end 100p of implant 100. In doing so, proximal set screw 40 pushes proximal wedge 60 towards proximal end 100p. Due to the inclination of superior ramps 64 and inferior ramps 63, the superior and inferior endplates 10, 20 are pushed apart at the proximal end 100p. For example, superior ramps 64 may slide along proximal ramps 18 of superior endplate 10 and inferior ramps 63 may slide along proximal ramps 28 of inferior endplate 20. In this way, set screw 40 linearly translates proximal wedge 60 such that superior and inferior ramps 64, 63 act against the superior and inferior endplates 10, 20 to urge them apart from one another at the proximal end 100p of implant 100.

Figure 15:
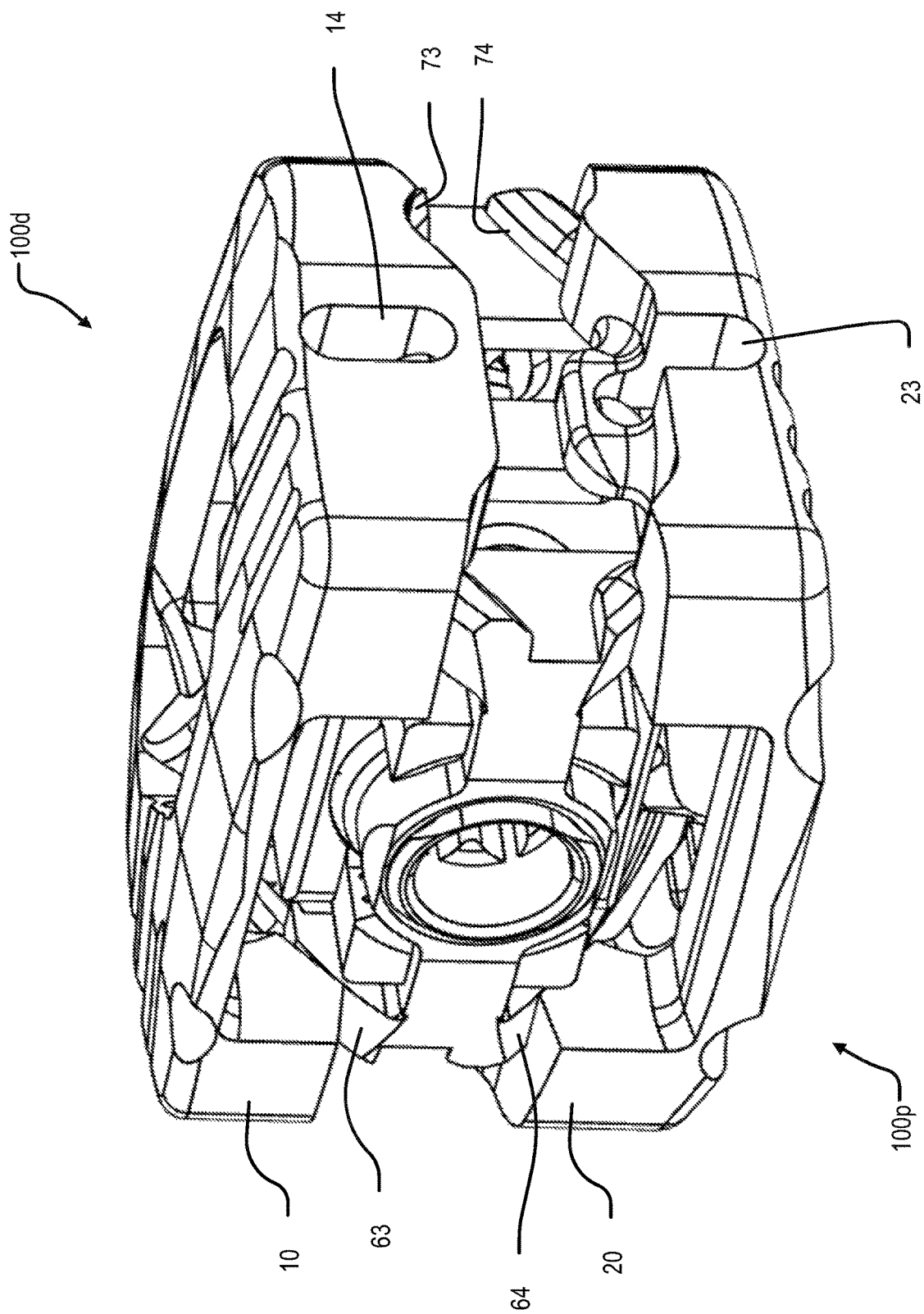
FIG. 15 is a front perspective view of an expandable implant in a second expanded configuration.
Figure 16:
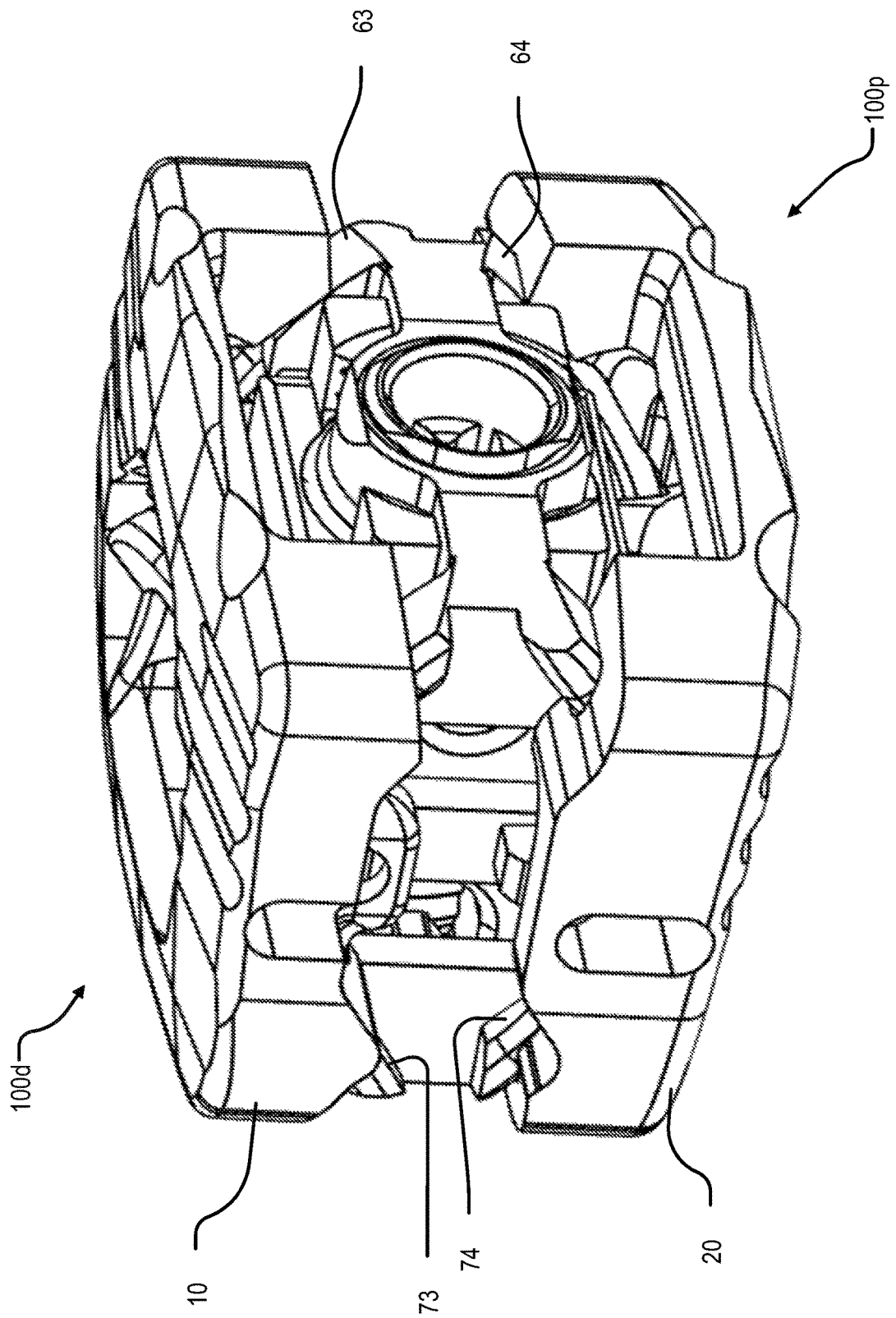
FIG. 16 is an alternate front perspective view of an expandable implant in a second expanded configuration.

As shown in FIGS. 15-16, implant 100 may be distracted in a parallel manner where the superior and inferior endplates 10, 20 are substantially parallel to one another and/or a height between superior and inferior endplates 10, 20 is about the same at the proximal end 100p and distal end 100d of implant 100, for example. The distal end 100d of implant 100 may have been expanded as illustrated due to distal wedge 70 being moved towards the distal end 100d of implant 100 in the proximal-to-distal direction P-D, for example. Distal wedge 70 may have moved towards the distal end 100d from a medial position due to distal set screw 50 being rotated within distal screw guide 31d such that distal set screw 50 is linearly translated towards distal end 100d of implant 100. In doing so, distal set screw 50 pushes distal wedge 70 towards distal end 100d. Due to the inclination of superior ramps 74 and inferior ramps 73, the superior and inferior endplates 10, 20 are pushed apart at the distal end 100d. For example, superior ramps 74 may slide along distal ramps 19 of superior endplate 10 and inferior ramps 73 may slide along distal ramps 29 of inferior endplate 20. In this way, set screw 50 linearly translates distal wedge 70 such that superior and inferior ramps 74, 73 act against the superior and inferior endplates 10, 20 to urge them apart from one another at the distal end 100d of implant 100.

Figure 17:
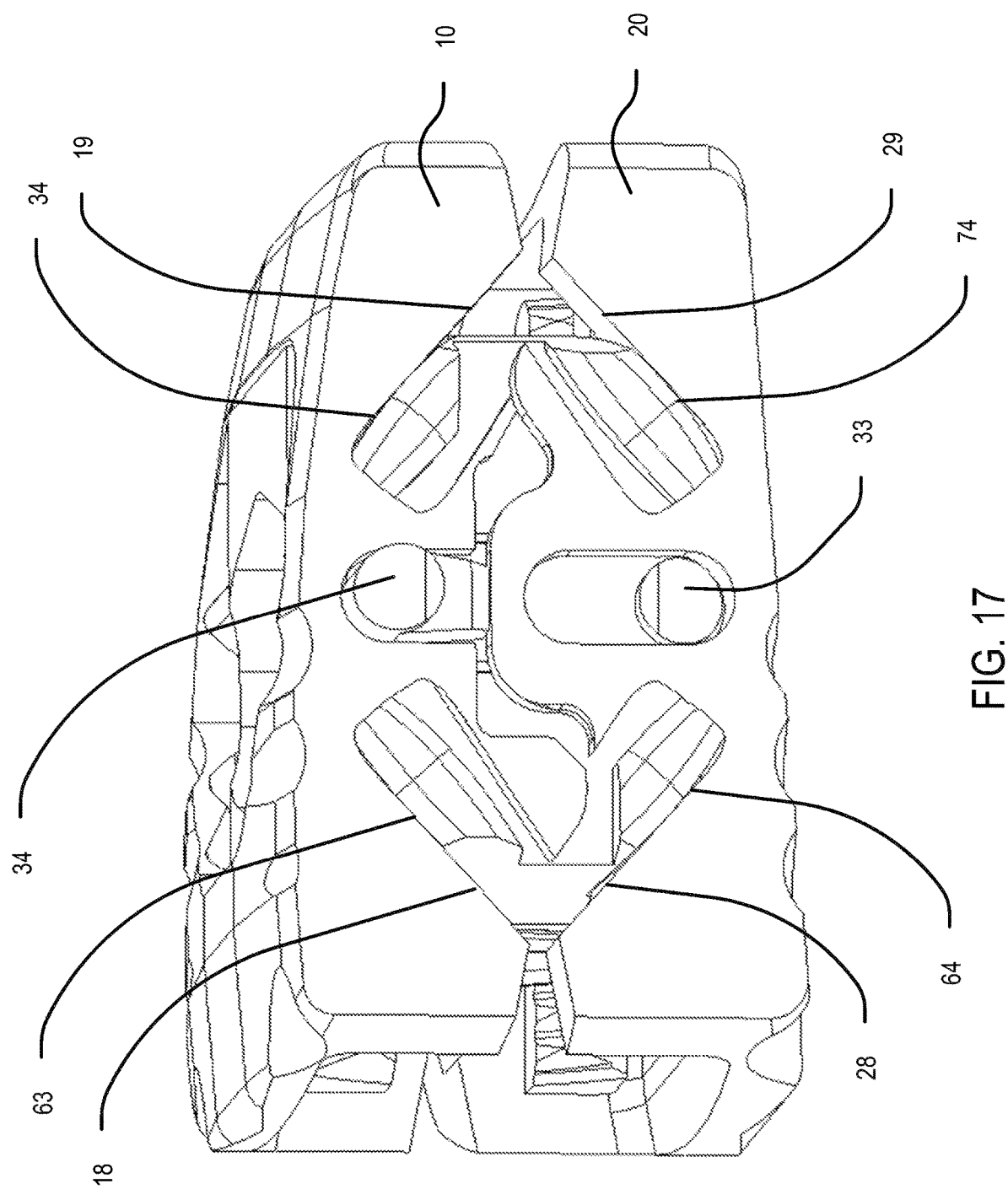
FIG. 17 is a perspective view of a cross section cut of an expandable implant in a contracted configuration.
Figure 18:
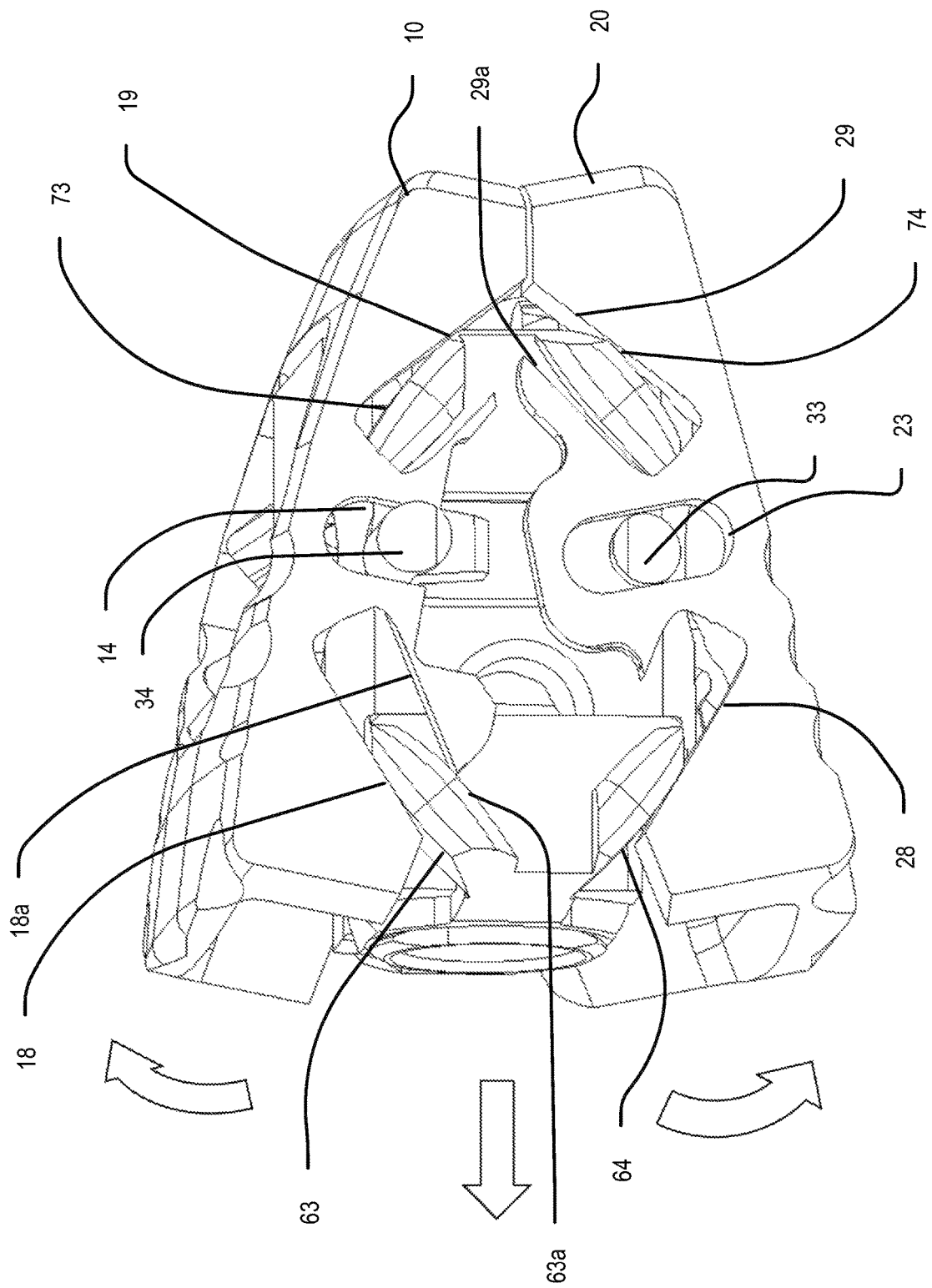
FIG. 18 is a perspective view of a cross section cut of an expandable implant in an expanded configuration.

Referring generally to FIGS. 17-20, various cross section views of an expandable implant 100 in a contracted configuration and an expanded configuration are shown. As shown in FIG. 17, implant 100 is in a contracted position and each of the proximal wedge 60 and distal wedge 70 are in a medial position. Furthermore, posts 34, 33 of support block 30 are engaged with the superior and inferior endplates 10, 20 by extending through slots 14, 23, respectively. As shown in FIG. 18, posts 34, 33 of support block 30 have changed a relative position within slots 14, 23 (relative to FIG. 17) to accommodate the increase in height at the proximal end 100p. For example, posts 34, 33 are fixed to support block 30 and the superior and inferior endplates 10, 20 may have expanded relative to support block 30 and therefore posts 34, 33 are shown in a different position relative to slots 14, 23. In FIG. 18, proximal wedge 60 may have moved towards the proximal end 100p due to proximal set screw 40 being rotated and thereby pushing proximal wedge 60 towards proximal end 100p, for example. Additionally, superior ramps 64 and inferior ramps 63, may act against the superior and inferior endplates 10, 20 to push them apart. For example, superior ramps 64 may slide along proximal ramps 18 of superior endplate 10 and inferior ramps 63 may slide along proximal ramps 28 of inferior endplate 20. In this way, set screw 40 linearly translates proximal wedge 60 towards proximal end 100p such that superior and inferior ramps 64, 63 act against the superior and inferior endplates 10, 20 to urge them apart from one another. Additionally, in some embodiments lower proximal ramps 18a may be provided at the proximal end of superior endplate 10. Lower proximal ramps 18a may act as a catch surface such that when set screw 40 is rotated in the opposite direction a lower surface 63a of superior ramps 63 may push against lower proximal ramps 18a to facilitate closing of the implant 100, for example.

Figure 19:
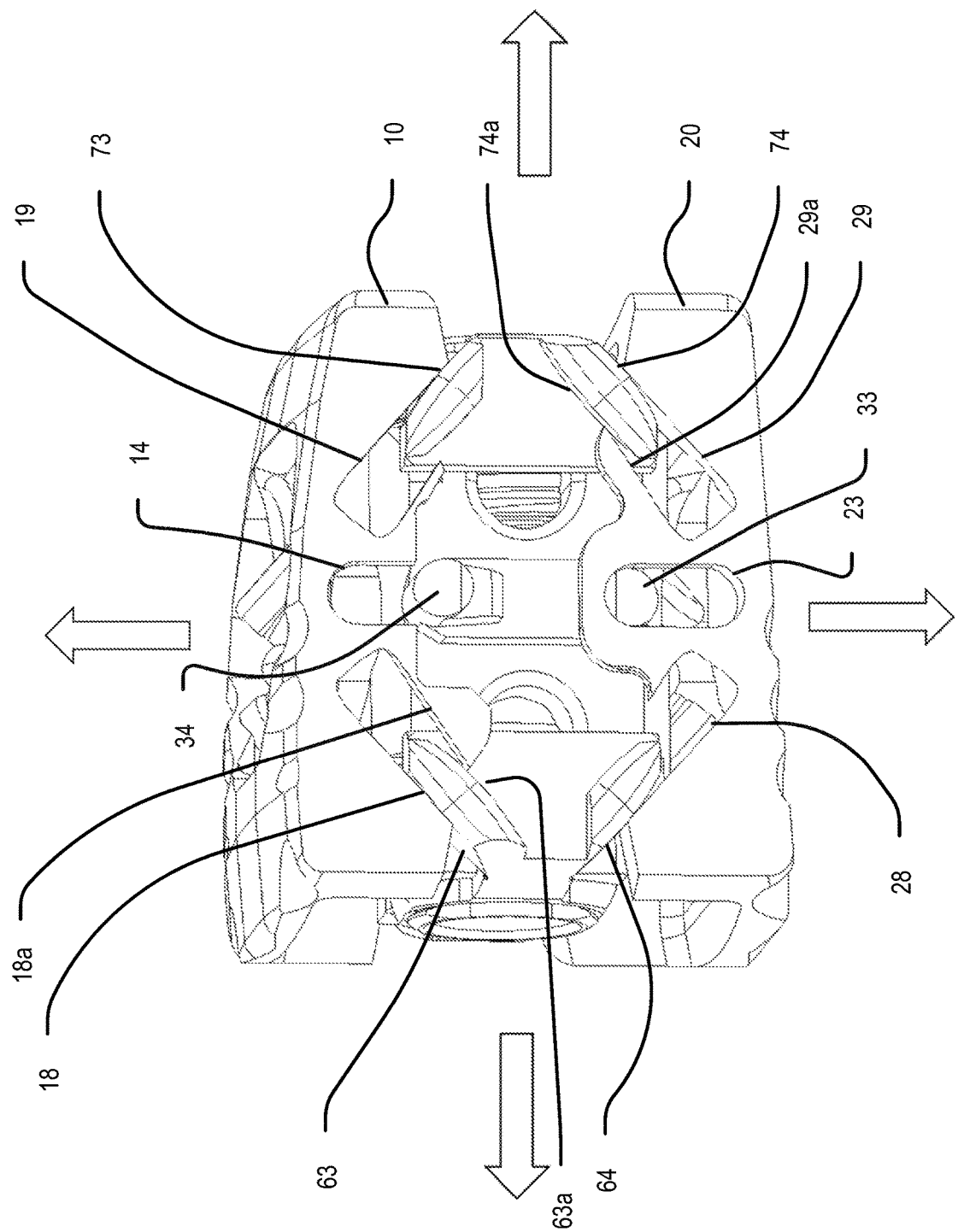
FIG. 19 is a perspective view of a cross section cut of an expandable implant in an expanded configuration.
Figure 20:
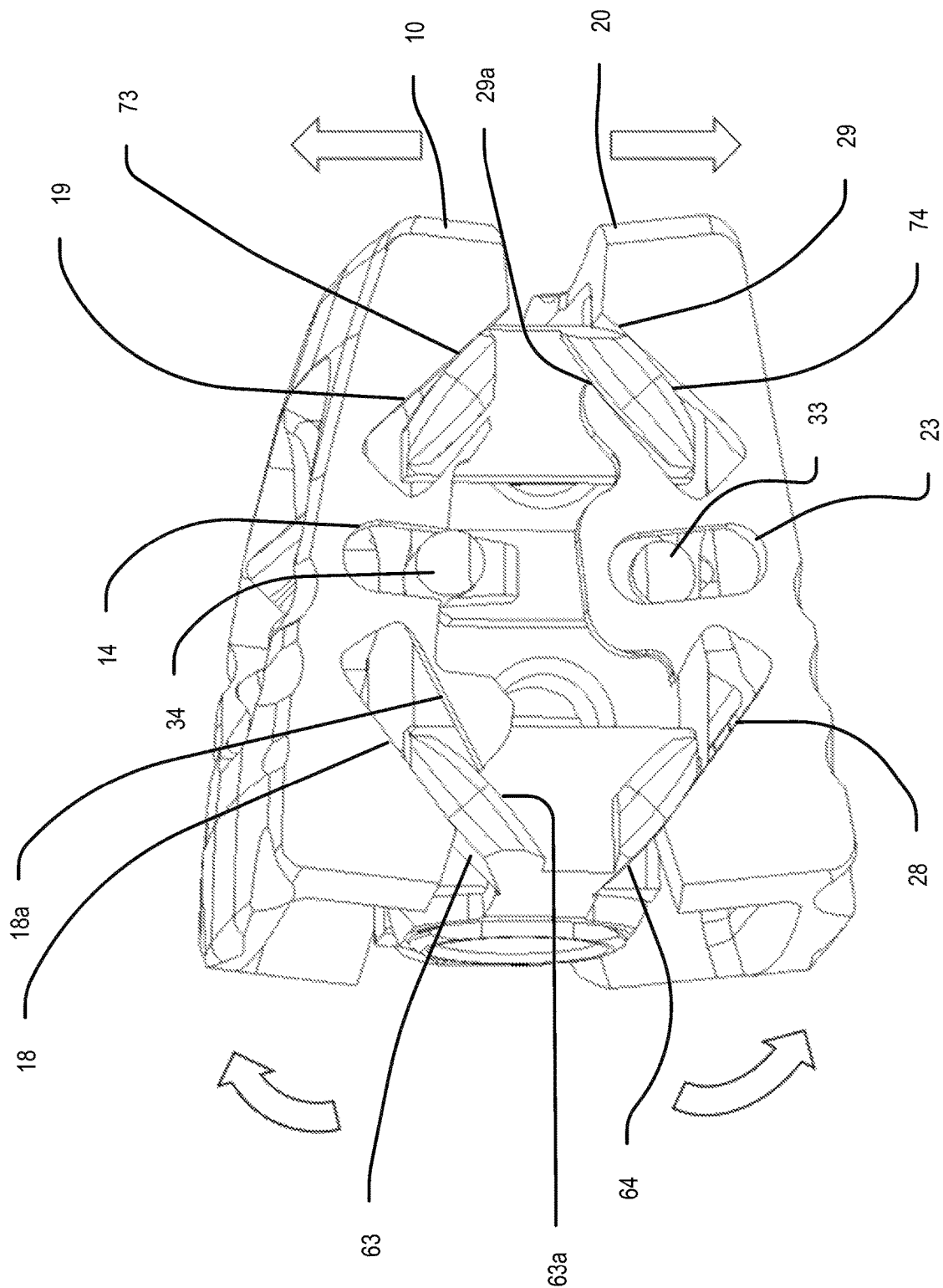
FIG. 20 is a perspective view of a cross section cut of an expandable implant in an expanded configuration.
Figure 21:
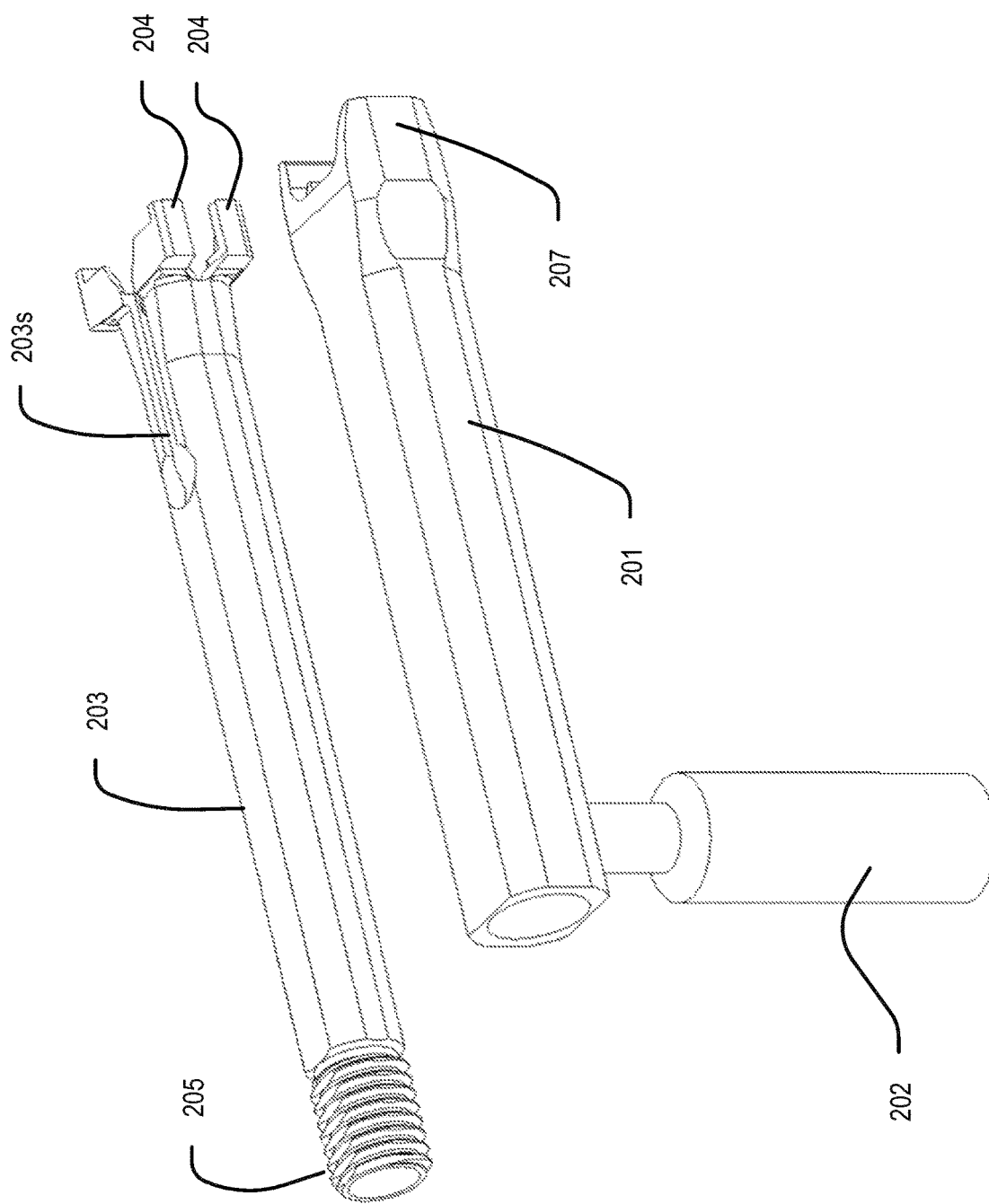
FIG. 21 is a perspective view of an inserter tool for use with disclosed expandable implants.

FIG. 19 is a cross section drawing through line C-C of FIG. 2. As shown in FIG. 19, posts 34, 33 of support block 30 have changed a relative position within slots 14, 23 (relative to FIG. 18) to accommodate the increase in height at the distal end 100d. For example, post 34 has moved through slot 14 to a lower position and post 33 has moved to an upper position within slot 23. With reference back to FIG. 15, slots 14, 23 extend in a lateral direction and posts 34, 14 are engaged within slots 14, 23 throughout the full range of expansion (although it may appear that in FIGS. 18-19 slot 14 is open at a bottom end this is due to the section being drawn through line C-C of FIG. 2, for example). In this way, support block 30 may remain coupled to implant 100. Additionally, distal wedge 70 may have moved towards the distal end 100d due to distal set screw 50 pushing distal wedge 70 towards distal end 100d. Additionally, superior ramps 74 and inferior ramps 73 may act against the superior and inferior endplates 10, 20 and push them apart at the distal end 100d. For example, set screw 50 linearly translates distal wedge 70 such that superior and inferior ramps 74, 73 act against the superior and inferior endplates 10, 20 to urge them apart from one another at the distal end 100d of implant 100. In some embodiments, upper distal ramps 29a may act as a catch surface such that when set screw 50 is rotated in the opposite direction an upper surface 74a of inferior ramps 74 may push against upper distal ramps 29a to facilitate closing of the implant 100, for example. For example, as shown in FIG. 20, a height between the superior and inferior endplates 10, 20 at distal end 100d is less than a height between the superior and inferior endplates 10, 20 at distal end 100d of FIG. 19. This may occur due to distal wedge 70 being moved in the proximal-to-distal direction towards a medial position of implant and upper distal ramps 29a acting as a catch surface as explained above, for example Those with skill in the art will appreciate that implant 100 is continuously adjustable at any level of distraction and/or lordosis between the fully collapsed position (see FIG. 17) and a fully expanded position (see FIG. 19).

Figure 22:
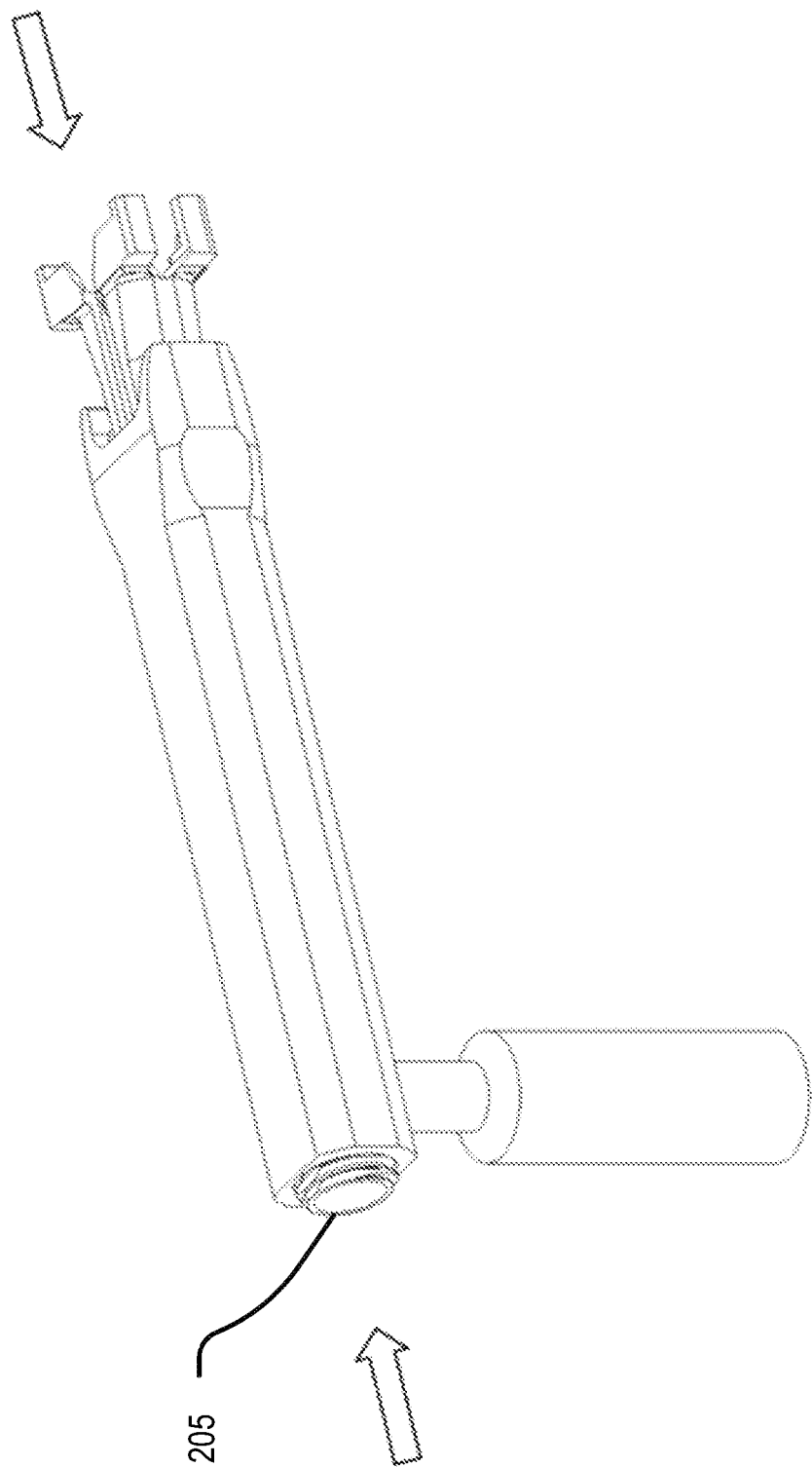
FIG. 22 is a perspective view of an inserter tool for use with disclosed expandable implants.
Figure 23:
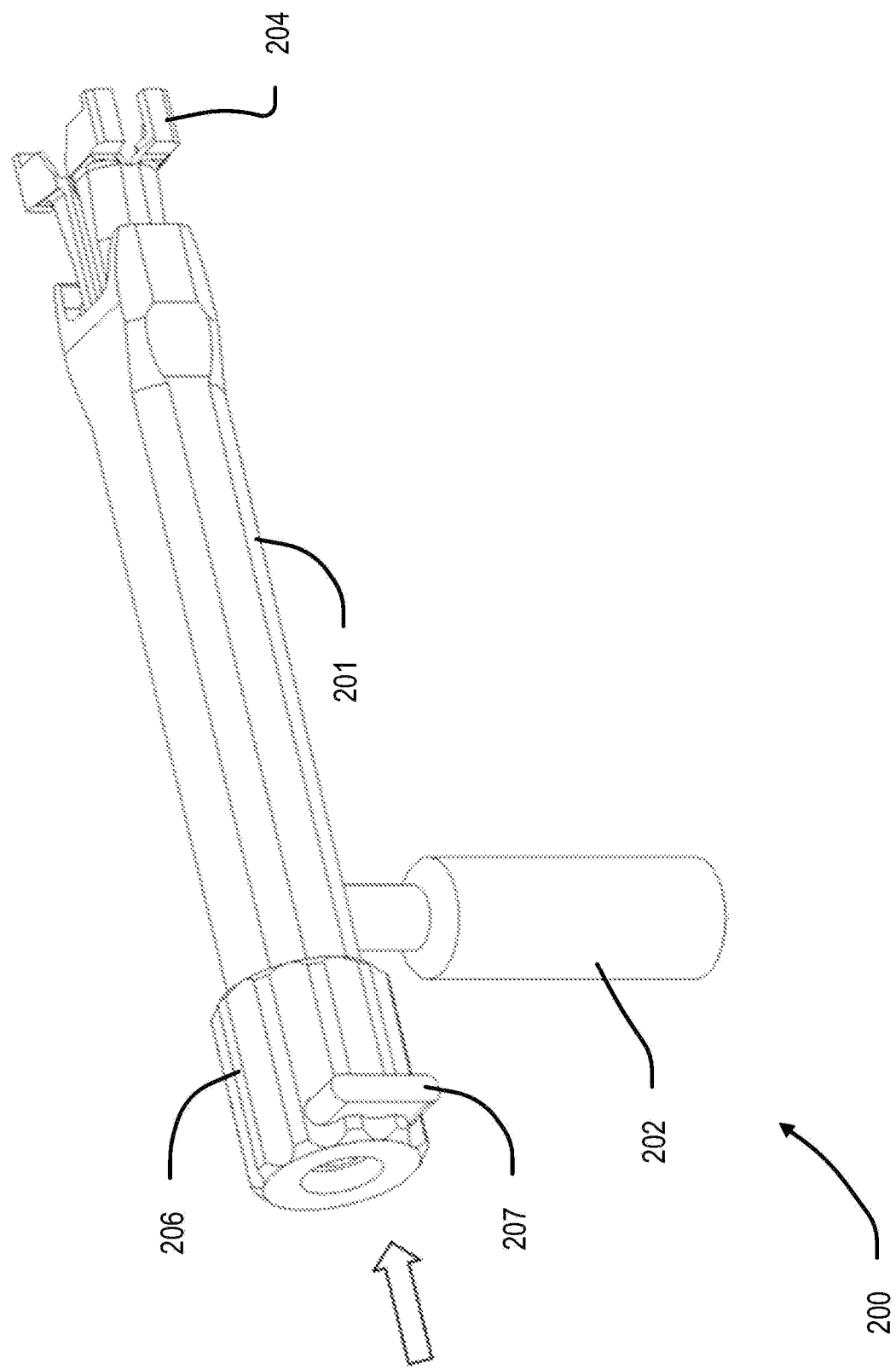
FIG. 23 is a perspective view of an inserter tool for use with disclosed expandable implants.
Figures 24A, 24B:
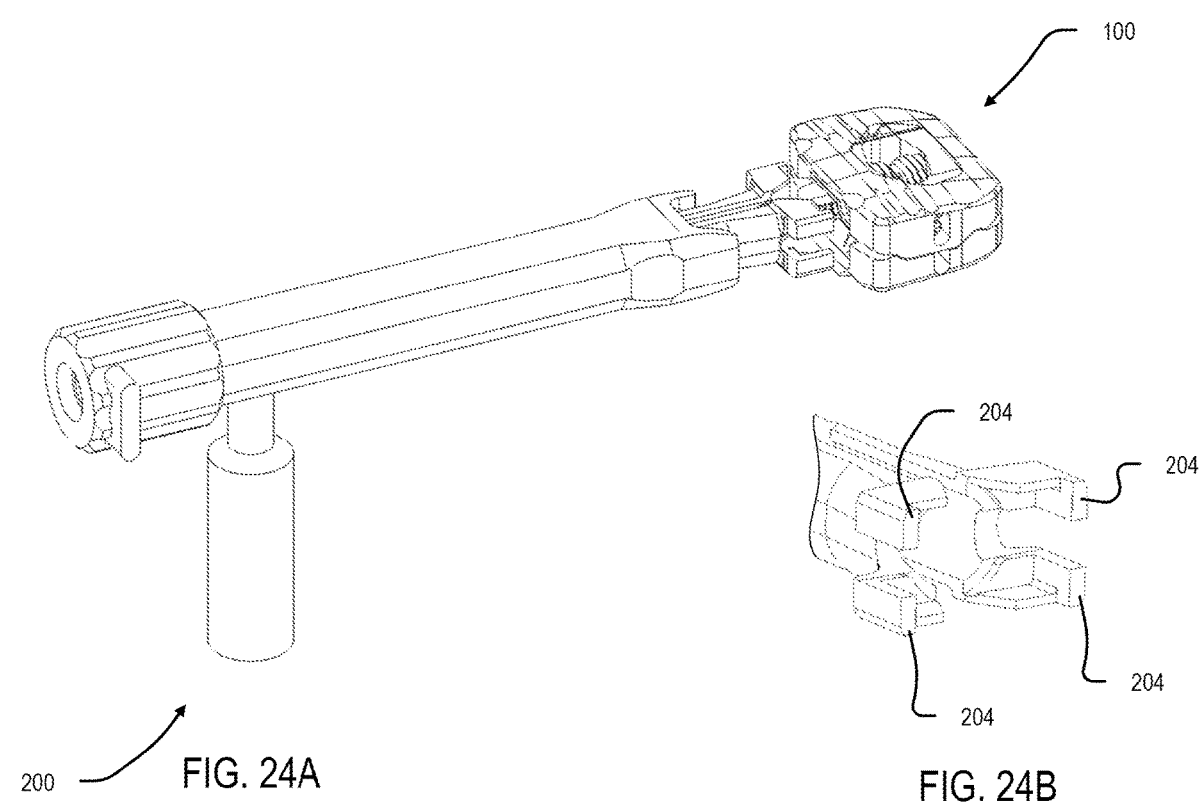
FIG. 24A is a perspective view of an inserter tool for use with disclosed expandable implants.
FIG. 24B is a perspective view of a distal region of an inserter tool for use with disclosed expandable implants.
Figure 25:
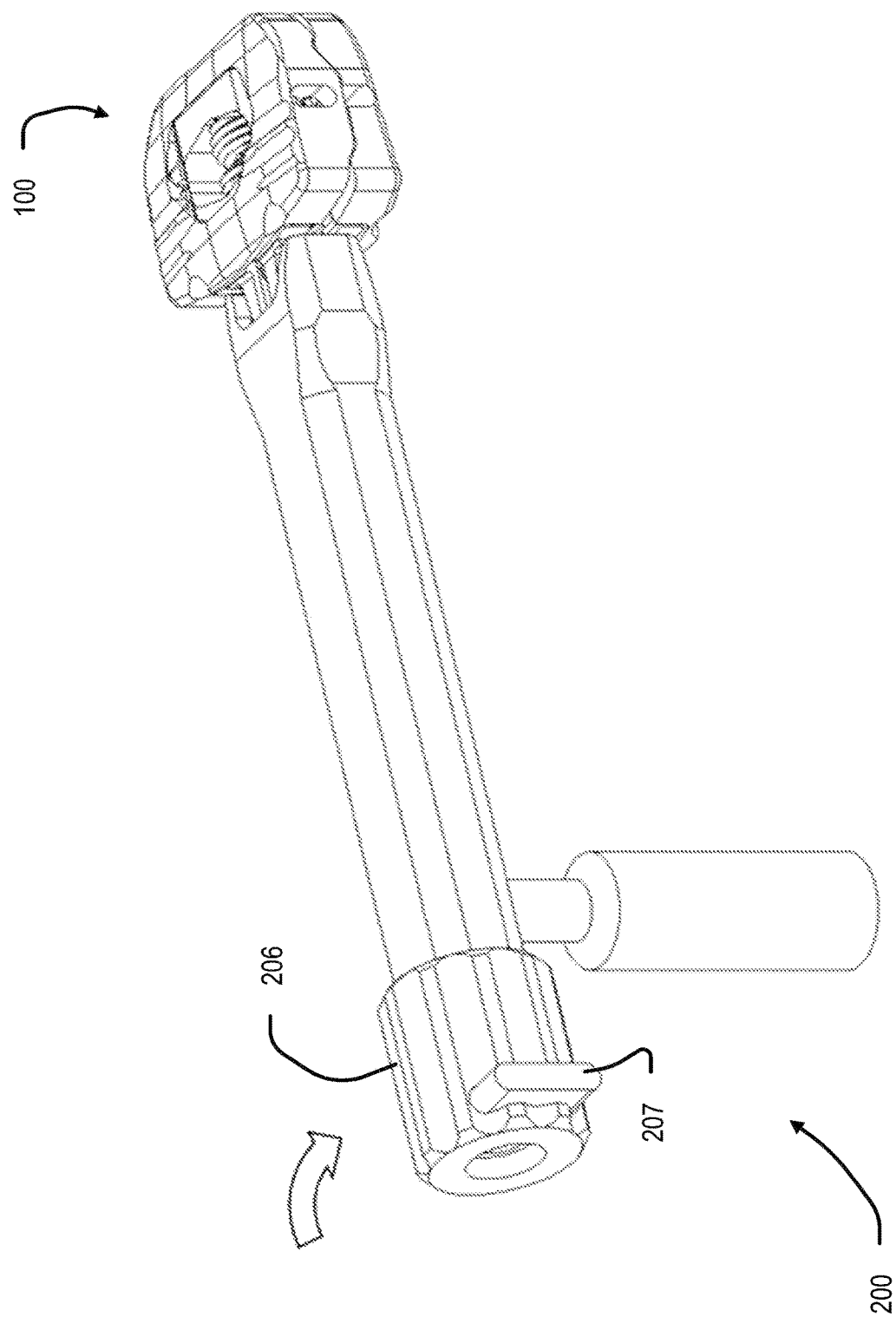
FIG. 25 is a perspective view of an inserter tool coupled to an expandable implant.

Referring generally to FIGS. 21-28B various views of an inserter tool 200 and a drive tool 300 for use with disclosed expandable implants 100 are shown. Inserter tool 200 may extend from a proximal end to distal end and include a hollow outer shaft 201 and a hollow inner shaft 203. The hollow outer shaft 201 may include support walls 207 at a distal end thereof having a size and shape close the flexible tip of shaft 203. For example, seam 203s may enable the distil end of shaft 203 to be compressed together when shaft 203 is insert within outer shaft 201 such that engagement arms 204 are moved closer together. Hollow outer shaft 201 may include a gripping handle 202 extending therefrom and in various embodiments, gripping handle 202 may be a stationary handle or a movable handle (not illustrated). Additionally, hollow inner shaft 203 may include engagement arms 204 at a distal end thereof, for example Engagement arms 204 may be used to grip implant 100 at engagement prongs 32, for example (see FIGS. 24A and 24B). Additionally, engagement arms 204 may have a size and shape generally corresponding to a size and shape of engagement prongs 32. For example, engagement arms 204 may surround (or at least partially surround) engagement prongs 32 and securely grip engagement prongs 32 such that implant 100 may be retained by inserter tool 200 and inserted into a disc space. In various embodiments, engagement arms 204 may have outdents and/or protrusions that engage corresponding grooves and/or recesses of engagement prongs 32 (not illustrated). Inserter tool 200 may include a hollow outer shaft 201 and a hollow inner shaft 203. As shown in FIG. 22, hollow inner shaft 203 may be inserted within and disposed within hollow outer shaft 201, for example. Hollow inner shaft 203 may include a threaded end 205 at a proximal end thereof. Threaded end 205 may extend beyond the proximal end of hollow outer shaft 201 such that a coupling member 206 having an internal thread pattern corresponding to the threaded end 205 may be attached to a proximal end of hollow inner shaft 203. Once coupling member 206 is sufficiently tightened the hollow outer shaft 201 and hollow inner shaft 203 may be securely coupled. Additionally, as coupling member 206 is rotated, the inner shaft 203 is pulled deeper within outer shaft 205 such that a compressive force may be applied at the engagement arms 204 via interior surfaces of support walls 207 thereby providing a strong clamping force around engagement prongs 32 of implant 100 (see FIGS. 21-25).

Figure 26:
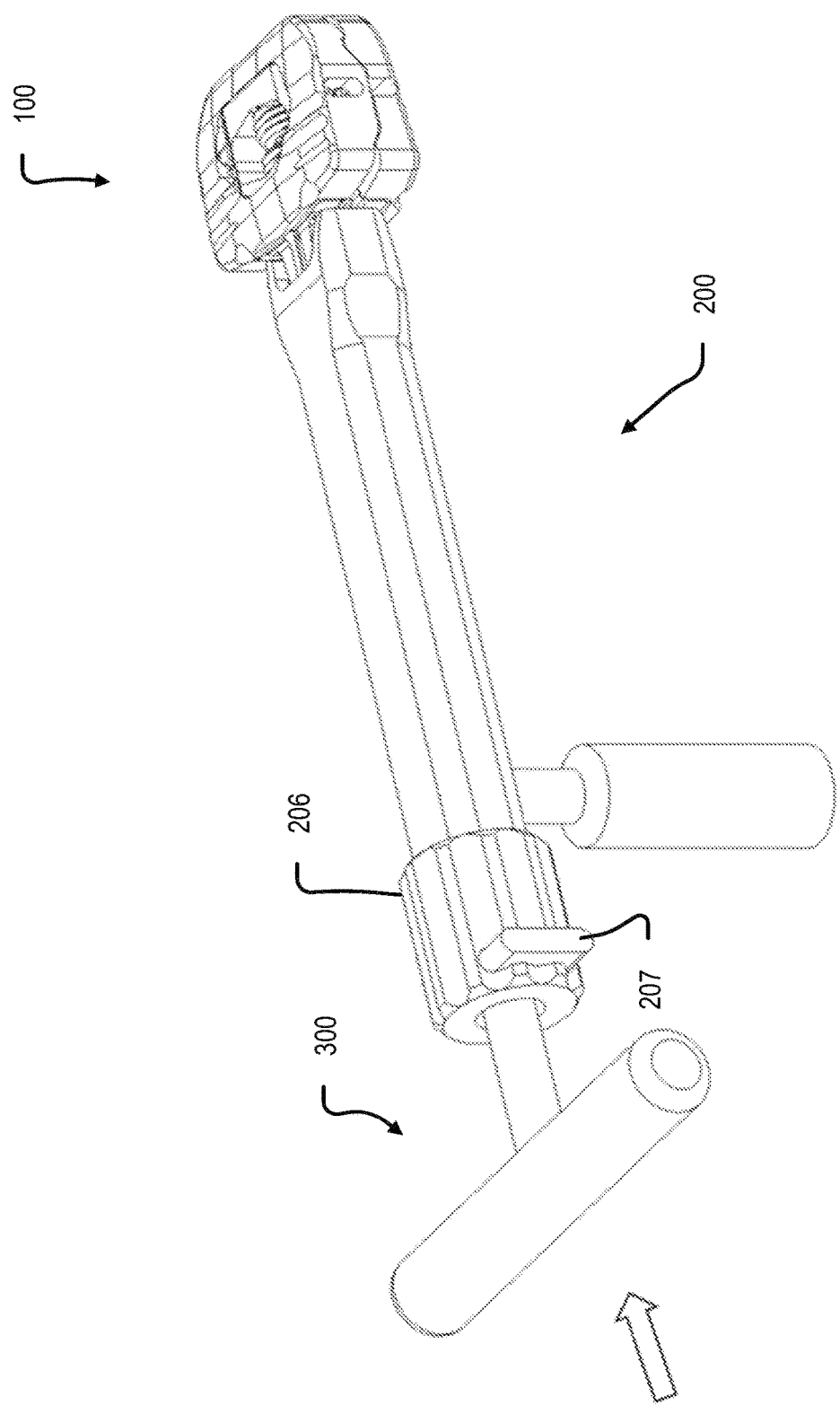
FIG. 26 is a perspective view of an inserter tool and a driver tool for use with disclosed expandable implants.
Figure 27:
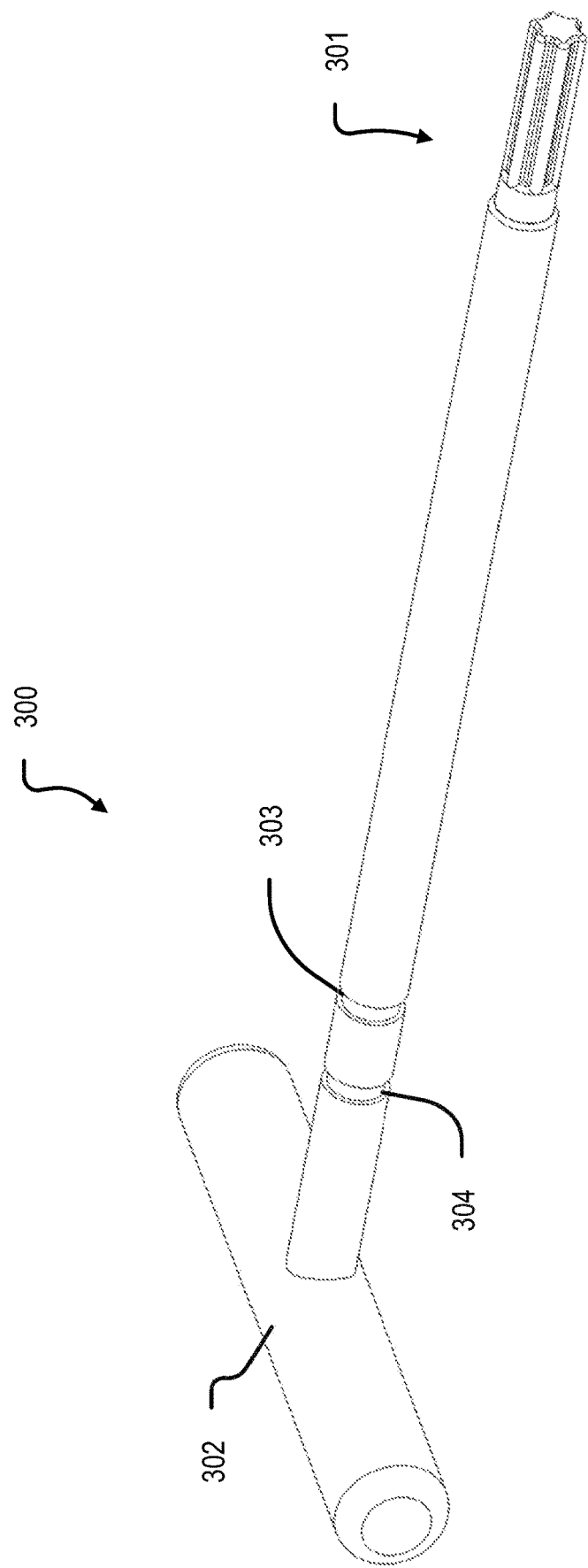
FIG. 27 is a perspective view of a drive tool for use with disclosed expandable implants.
Figure 28B:
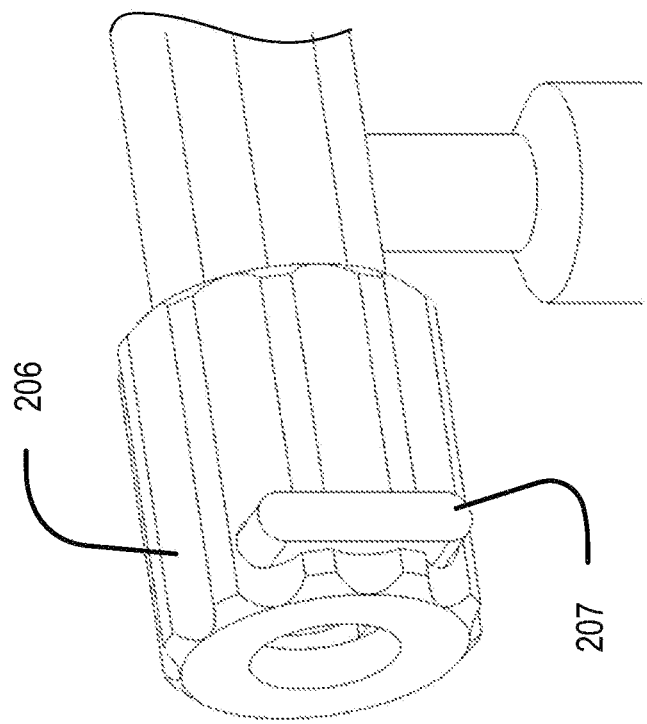
FIG. 28B is an enlarged view of a proximal end of an inserter tool in a locked position.
Figure 28A:
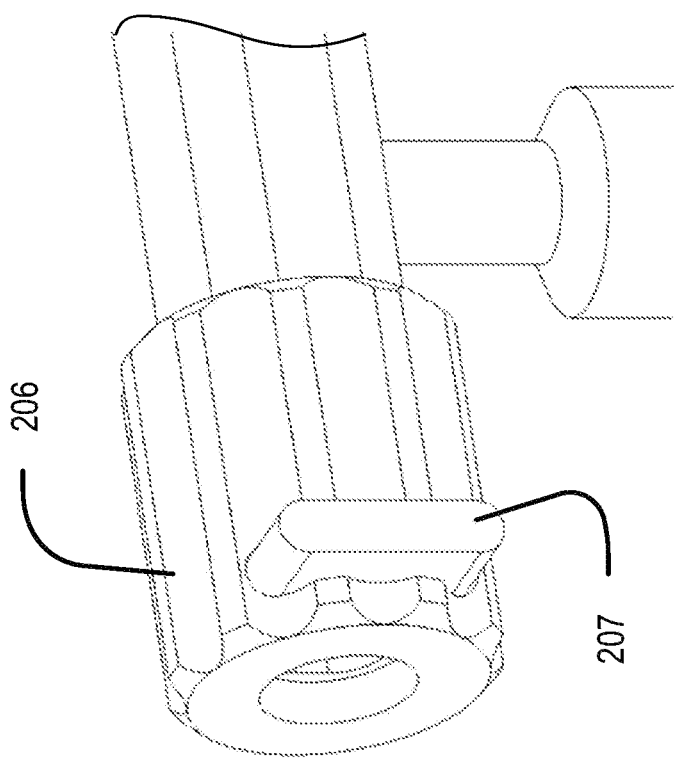
FIG. 28A is an enlarged view of a proximal end of an inserter tool in an unlocked position.

Once the coupling member 206 is sufficiently tightened such that engagement arms 204 are secured to engagement prongs 32, a drive tool 300 may be inserted through an aperture of coupling member 206 and into the hollow interior of inner shaft 203 (see FIG. 26). Drive tool 300 may extend in a proximal to distal direction and include a handle 302 at a proximal end and a drive end 301 at a distal end, for example. Additionally, drive tool 300 may include a first circumferential channel 303 and a second circumferential channel 304 that may be indented along an outside surface of drive tool 300. In the example, embodiment, a depressible lock 207 of coupling member 206 may selectively engage and disengage with either one of the first circumferential channel 303 and a second circumferential channel 304 to position drive tool 300 at relative axially aligned positions within the interior of hollow interior shaft 203. For example, as shown in FIG. 28A depressible lock 207 is disengaged and as shown in FIG. 28B depressible lock 207 is depressed such that an indent or the like may b retained circumferential channels 303 or 304. A relative distance between the first circumferential channel 303 and a second circumferential channel 304 may correspond to a distance between the proximal set screw 40 and distal set screw 50, for example.

Figure 29:
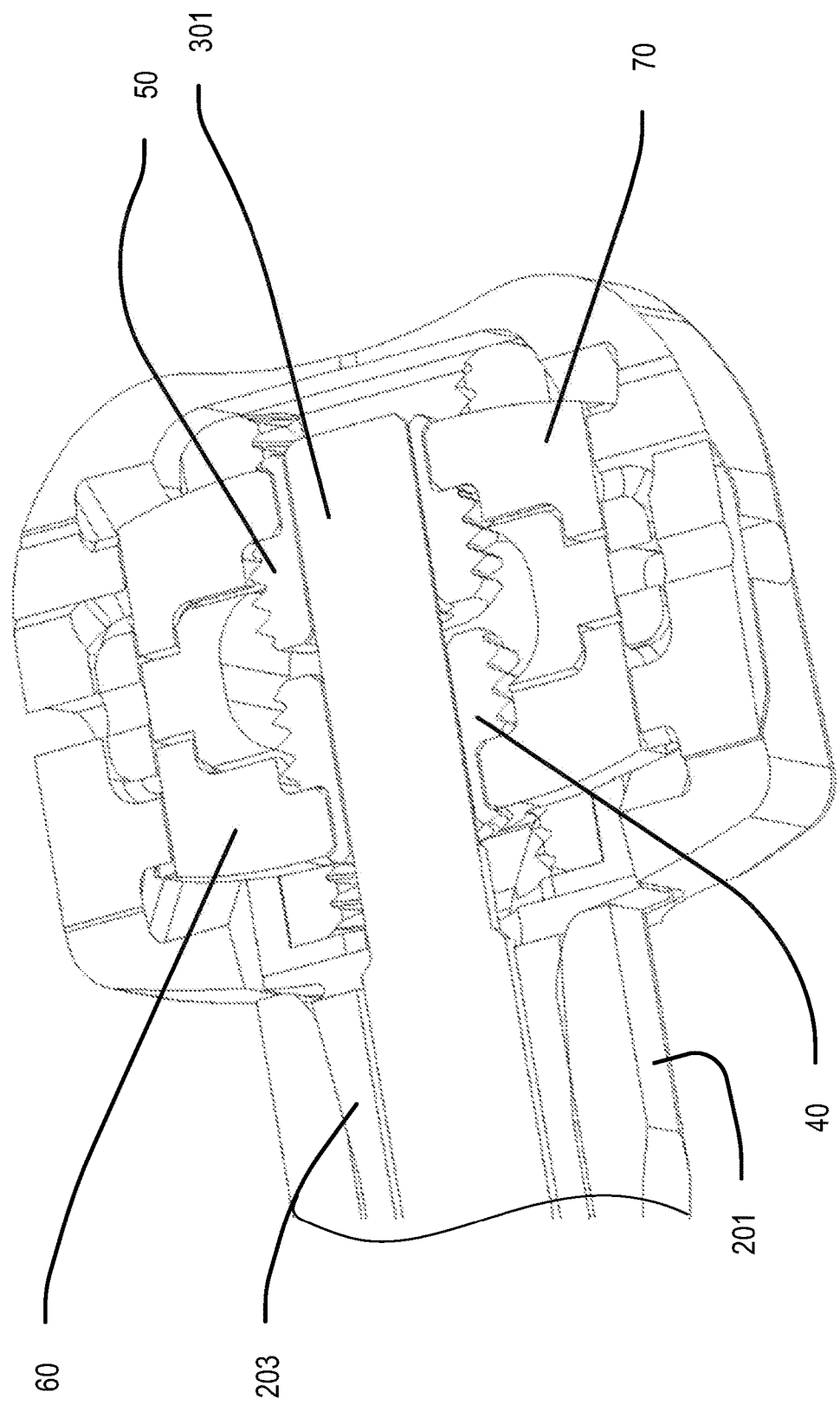
FIG. 29 is a cross section cut showing an inserter tool and a drive tool operably engaged with an expandable implant.
Figure 30:
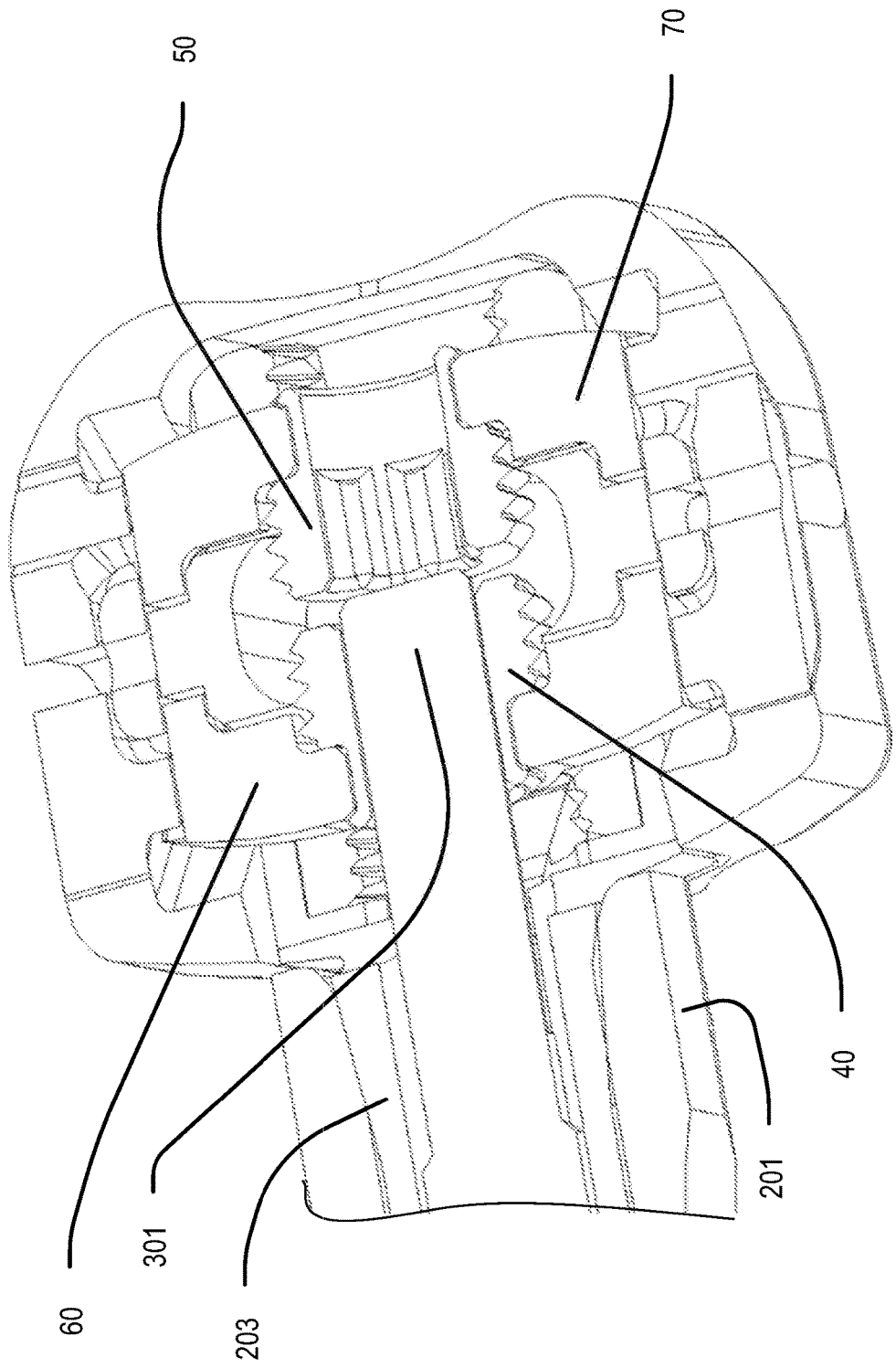
FIG. 30 is a cross section cut showing an inserter tool and a drive tool operably engaged with an expandable implant.

In this way, toggling between engaging the depressible lock 207 with either one of the first and second circumferential channels 303, 304 may affect whether drive end 301 engages with both the distal set screw 50 and proximal set screw 40 or alternatively just the proximal set screw 40, for example. As shown in FIG. 29, the depressible lock 207 may be engaged with the second circumferential channel 304 such that drive end 301 may simultaneously drive both the distal set screw 50 and proximal set screw 40. As shown in FIG. 30, the depressible lock 207 may be engaged with the first circumferential channel 303 such that drive end 301 is only engaged with the proximal set screw 40. At least one advantage of this configuration is that an end user such as a surgeon may simultaneously rotate the proximal and distal set screws 40, 50 to cause parallel distraction or rotate only the proximal set screw 40 to cause lordosis.

Figure 31:
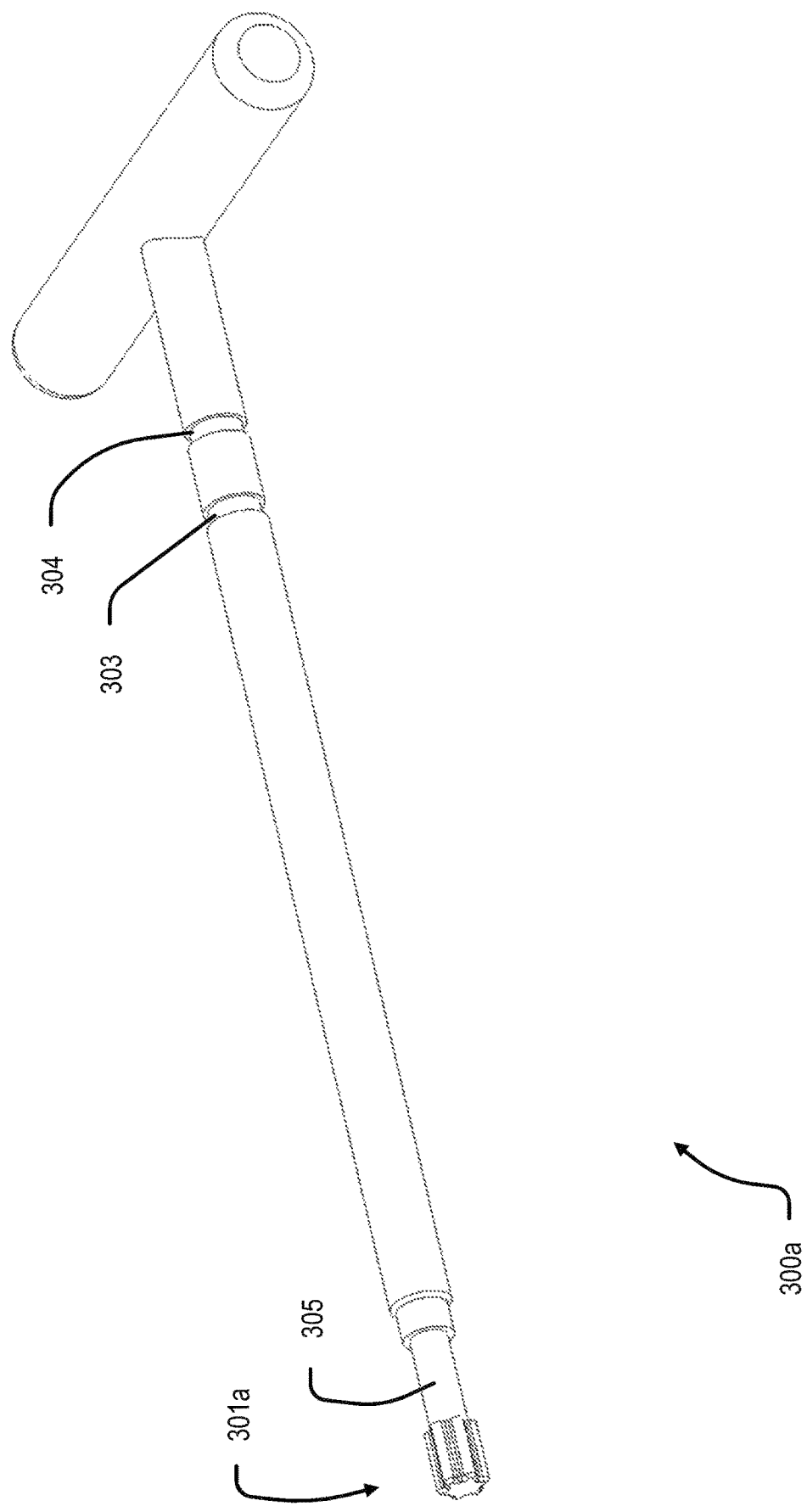
FIG. 31 is a perspective view of an alternate drive tool for use with disclosed expandable implants.
Figure 32:
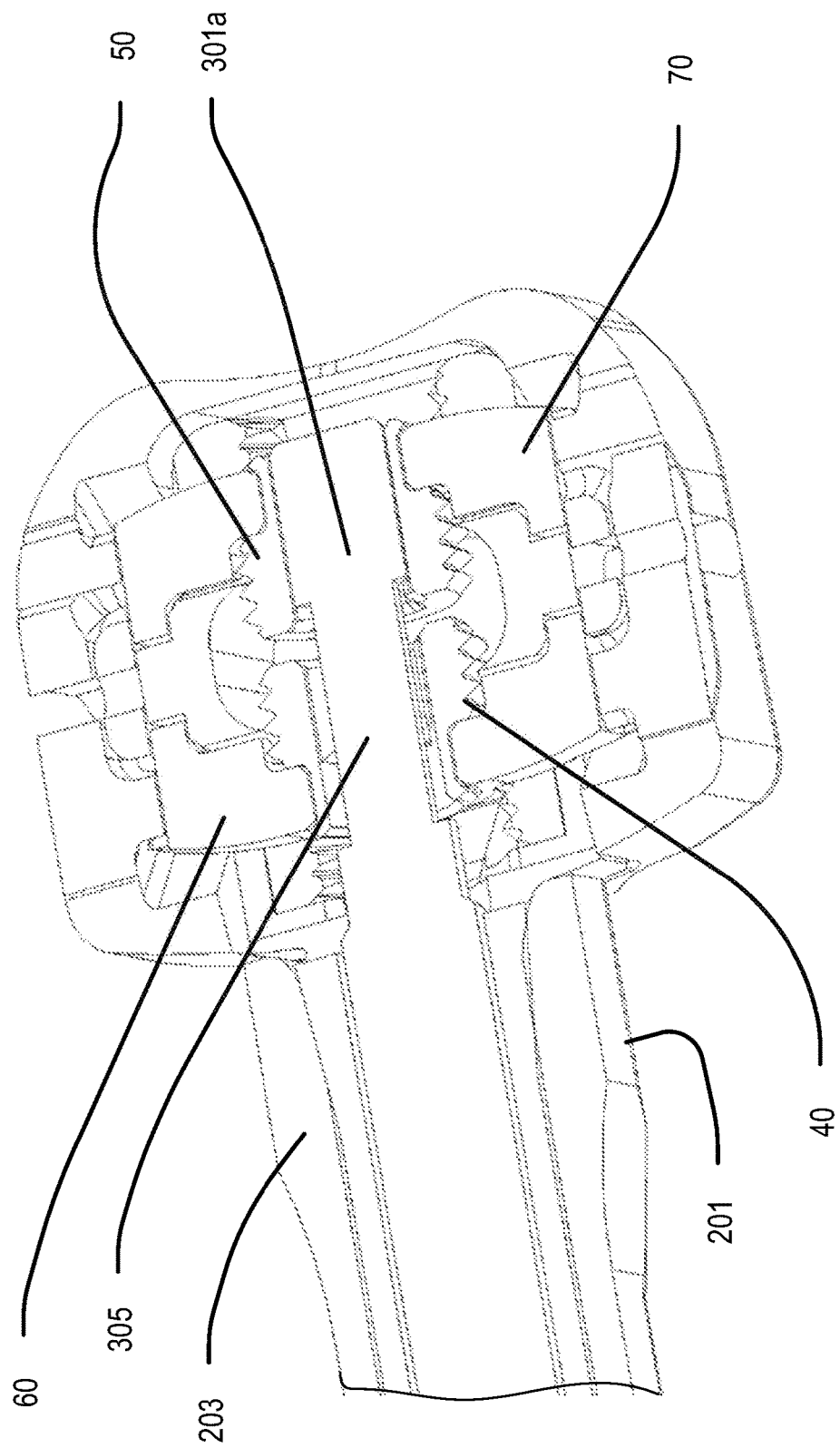
FIG. 32 is a cross section cut of the alternate drive tool of FIG. 31 engaged with an expandable implant.

FIG. 31 illustrates an alternate drive tool 300a. Alternate drive tool 300a may include the same, substantially the same, and or similar characteristics as explained above with respect to drive tool 300. However, alternate drive tool 300a may include a necked down portion 305 and a drive end 301a having a size and shape suitable for only engaging one of the proximal set screw 40 or distal set screw 50 at a time. For example, the necked down portion 305 may have a smaller cross sectional diameter (thickness) than the drive end 301a. This arrangement may be particularly advantageous for engaging only the distal set screw 50 to change a relative height between the superior and inferior endplates 10, 20 at the distal end 100d only, for example. As shown in FIG. 32, drive end 301a is only engaged with the distal set screw 50 and the necked down portion 305 is narrow enough such that it does not contact the interior circumferential surface of set screw 40, for example. Similarly, this arrangement may be particularly advantageous for engaging only the proximal set screw 40 to change a relative height between the superior and inferior endplates 10, 20 at the proximal end 100p only, for example. Furthermore, when engaging only distal set screw 50, a relative height between the superior and inferior endplates 10, 20 at the distal end 100d may be changed, for example to create kyphosis.

Figure 33:
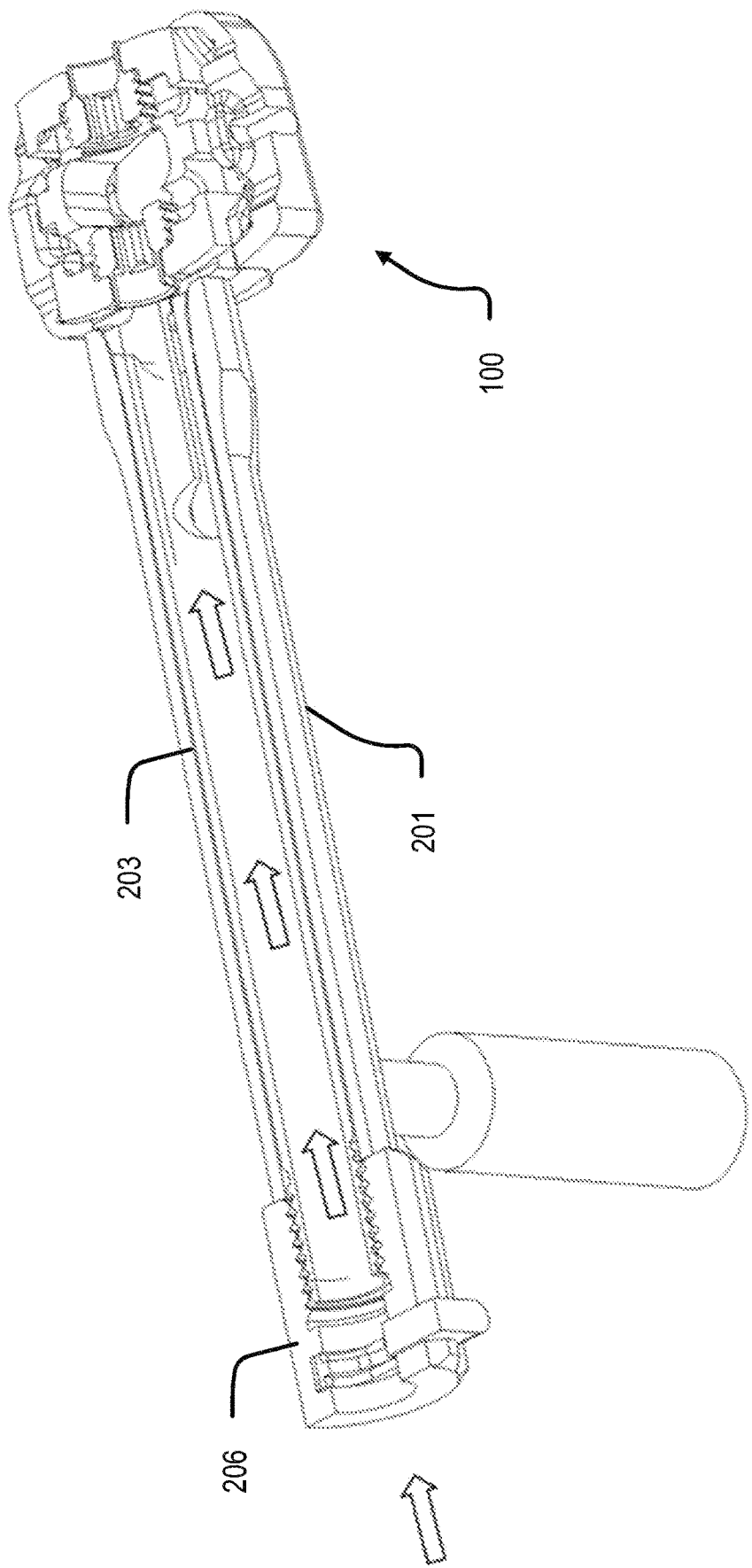
FIG. 33 is a cross section cut of an inserter tool and an example method of use of the inserter tool.

In some embodiments, after implant 100 is expanded into a target configuration suitable for a particular patient, bone graft material (BGM) may be injected into implant 100. For example, flowable bone graft material may be injected under pressure. For example, as shown in FIG. 33, the drive tool 300 (or alternate drive tool 300a) may be removed from within the hollow interior of inner shaft 203. Thereafter, bone growth promoting material may be injected through the hollow interior of inner shaft 203 and into the interior of implant 100. For example, bone growth promoting material may flow through shaft 203, through set screw 40, through a central cavity of block support block 30 and into contact with the endplates of adjacent vertebrae. Additionally, lateral holes between posts 34, 33 of support block 30 may allow additional bone growth promoting material to flow out in a lateral direction and into the interior of implant 100 and to surround wedges 60, 70. In this way, the entire interior space of implant 100 may be filled with bone growth promoting material to promote fusion. In some embodiments, flexible curtains (not illustrated) may extend from superior endplate 10 and/or inferior endplate 20 across gaps that may be created between endplates 10, 20 due to expanding the endplates. In some embodiments, a distal most end of distal set screw 50 may also be closed to prevent material from flowing out of distal set screw 50. Additionally, and depending on the type of surgery performed and the various patient anatomy that may contact the implant 100, curtains may not be required, as the patient anatomy would provide a retaining surface to keep material within implant 100.

Figure 34:
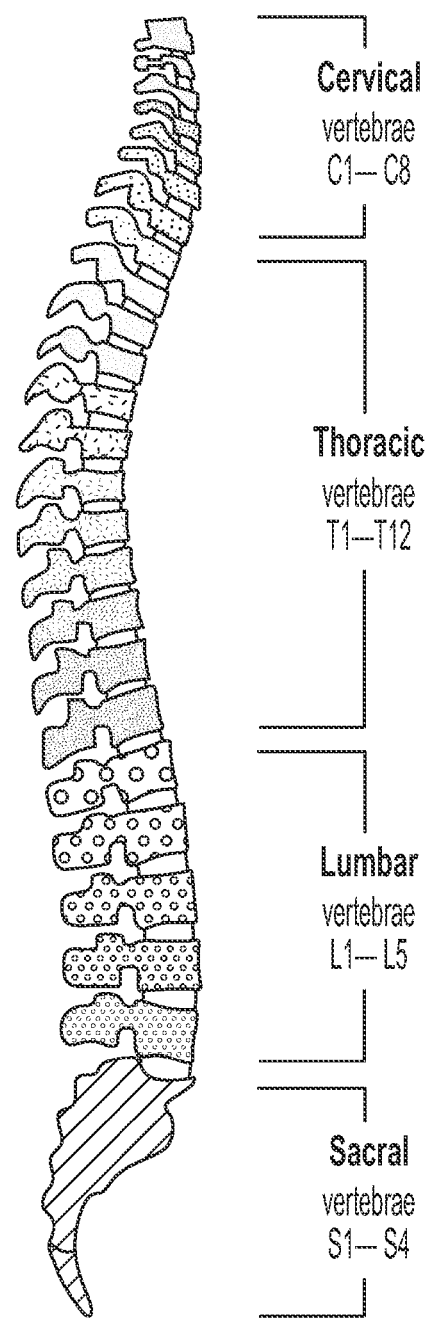
Figure 35:
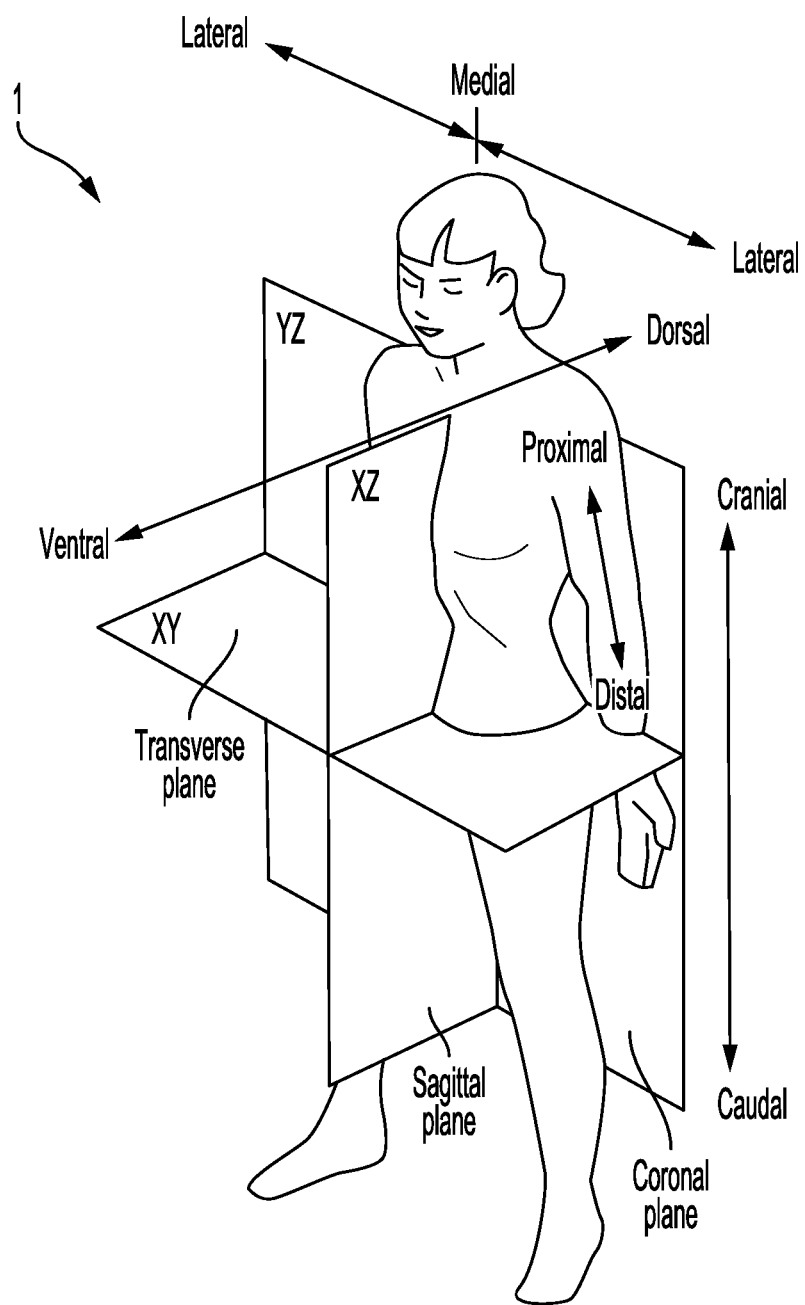

FIG. 34 is a reference drawing showing the human spine of which various disclosed implant embodiments may be installed in. FIG. 35 is a reference drawing showing various planes and reference directions of which the various disclosed implant embodiments may move in or act in with reference to a patient 1.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/ or "comprising," when used in this specification, specify the presence of stated features, elements, and/or components, but do not preclude the presence or addition of one or more other features, steps, operations, elements, components, and/or groups thereof.

What is claimed is:

1. An expandable implant movable between a contracted position and an expanded position, comprising:
    an expandable body extending from a proximal end to a distal end in a proximal-to-distal direction, extending from a first lateral side to a second lateral side in a widthwise direction, and extending from a superior end to an inferior end in a vertical direction, the expandable body being defined by a superior endplate and an inferior endplate opposite the superior endplate,
    the superior endplate including a first outside surface and a first inside surface opposite the first outside surface, the first inside surface including first proximal ramps and first distal ramps disposed opposite the first proximal ramps;
    the inferior endplate including a second outside surface and a second inside surface opposite the second outside surface, the second inside surface including second proximal ramps and second distal ramps disposed opposite the second proximal ramps;
    a support block coupled to the superior endplate and the inferior endplate, the support block having a proximal screw guide and a distal screw guide opposite the proximal screw guide,
    a proximal set screw rotatably supported by the proximal screw guide and a distal set screw rotatably supported by the distal screw guide;
    a proximal wedge including first superior ramped surfaces and first inferior ramped surfaces, the proximal wedge being coupled to the proximal set screw; and
    a distal wedge including second superior ramped surfaces and second inferior ramped surfaces, the distal wedge being coupled to the distal set screw;
    wherein:
        in a contracted position the proximal wedge and the distal wedge are disposed in a medial position within the expandable body,
        in a first expanded position a spacing between the superior and inferior endplates at thereof a proximal side is greater than a spacing between the superior and inferior endplates at the proximal side in the contracted position, wherein
        in the first expanded position the proximal wedge contacts the first proximal ramps and the second proximal ramps and is disposed proximate the proximal side, and
        in a second expanded position a spacing between the superior and inferior endplates at thereof a distal side is greater than a spacing between the superior and inferior endplates at the distal side in the contracted position, wherein in the second expanded position the distal wedge contacts the first distal ramps and the second distal ramps and is disposed proximate the distal side with respect to the medial position.

2. The expandable implant of claim 1, wherein the support block further includes a first post extending from a first lateral side thereof in the widthwise direction through a first slot of the superior endplate.

3. The expandable implant of claim 2, wherein the support block further includes a second post extending from a second lateral side thereof in the widthwise direction through a second slot of the inferior endplate.

4. The expandable implant of claim 3, wherein the first post and the second post extend in substantially opposite directions.

5. The expandable implant of claim 1, wherein:
the first inside surface of the superior endplate further comprises proximal catch surfaces and distal catch surfaces,
the proximal catch surfaces being adjacent to and inclined at substantially the same orientation as the first proximal ramps, and
the distal catch surfaces being adjacent to and inclined at substantially the same orientation as the first distal ramps.

6. The expandable implant of claim 5, wherein:
the first superior ramped surfaces are disposed between the first proximal ramps and the proximal catch surfaces, respectively.

7. The expandable implant of claim 6, wherein:
upper surfaces of the first superior ramped surfaces directly contact the first proximal ramps, respectively, and
lower surfaces of the first superior ramped surfaces directly contact the proximal catch surfaces, respectively.

8. The expandable implant of claim 1, wherein:
the proximal set screw includes a first flange that extends through a first annular aperture of the proximal wedge, and
the distal set screw includes a second flange that extends through a second annular aperture of the distal wedge.

9. The expandable implant of claim 8, wherein:
the proximal set screw further comprises a first contoured interior drive surface disposed on an opposite end from the first flange, and
the distal set screw further comprises a second contoured interior drive surface disposed on an opposite end from the second flange.

10. The expandable implant of claim 1, wherein:
the proximal set screw and distal set screw are coaxially aligned and each includes a contoured interior drive surface, and
a screw adjusting aperture extends through the proximal wedge, proximal set screw, support block, and distal set screw.

11. The expandable implant of claim 1, wherein:
a proximal end of the superior endplate comprises at least one first connection point configured to secure to a modular bone screw fixation plate; and
a proximal end of the inferior endplate comprises at least one second connection point configured to secure to a modular bone screw fixation plate.

12. The expandable spinal implant of claim 1, wherein the distal side of the superior endplate and inferior endplate each include a curved cutout.

13. The expandable spinal implant of claim 1, wherein the superior endplate is concave in the proximal-to-distal direction and concave in the widthwise direction.

14. The expandable spinal implant of claim 13, wherein the inferior endplate is concave in the widthwise direction only.

15. The expandable spinal implant of claim 1, wherein the support block further comprises a plurality of engagement prongs.

16. A spinal implant system, comprising:
the expandable spinal implant of claim 15, and
an insertion tool extending in a longitudinal direction from a proximal end to a distal end thereof, the insertion tool including a plurality of engagement arms having a size and shape corresponding to the plurality of engagement prongs.

17. The spinal implant system of claim 16, wherein the insertion tool further comprises a hollow outer shaft and a hollow inner shaft disposable within the hollow outer shaft, and the plurality of engagement arms are disposed on a distal end of the hollow inner shaft.

18. The spinal implant system of claim 17, further comprising:
a first set screw driving tool disposable within the hollow inner shaft and having a drive end having a first cross sectional diameter and a necked down portion having a second cross sectional diameter, the first cross sectional diameter being greater than the second cross sectional diameter,
wherein the first set screw driving tool is extendable in the longitudinal direction through the hollow interior shaft such that the drive end is engageable with either one of the proximal set screw or distal set screw.

19. The spinal implant system of claim 17, further comprising:
a second set screw driving tool disposable within the hollow inner shaft and having a drive end,
wherein the second set screw driving tool is extendable in the longitudinal direction through the hollow inner shaft such the drive end is engageable with both of the proximal set screw and distal set screw.

20. An expandable and contractable spinal implant, comprising:
an expandable body extending from a proximal end to a distal end in a proximal-to-distal direction, extending from a first lateral side to a second lateral side in a widthwise direction, and extending from a superior end to an inferior end in a vertical direction, the expandable body being defined by a superior endplate and an inferior endplate opposite the superior endplate;
the superior endplate including a first outside surface and a first inside surface opposite the first outside surface, the first inside surface including first proximal ramps and first distal ramps disposed opposite the first proximal ramps;
the inferior endplate including a second outside surface and a second inside surface opposite the second outside surface, the second inside surface including second proximal ramps and second distal ramps disposed opposite the second proximal ramps;
a support block coupled to the superior endplate and the inferior endplate, the support block having a proximal screw guide and a distal screw guide opposite the proximal screw guide, the proximal screw guide defining a first rotation axis and the distal screw guide defining a second rotation axis, the first and second rotation axes extending in the proximal-to-distal direction;

a proximal set screw rotatably supported by the proximal screw guide and a distal set screw rotatably supported by the distal screw guide;

a proximal wedge coupled to the proximal set screw and including first superior ramped surfaces and first inferior ramped surfaces, and a distal wedge coupled to the distal set screw and including second superior ramped surfaces and second inferior ramped surfaces, wherein:
the proximal wedge is coupled to the proximal set screw and movable toward and away from the proximal end of the expandable body in the proximal-to-distal direction by rotation of the proximal set screw along the first rotation axis, the distal wedge is coupled to the distal set screw and movable toward and away from the distal end of the expandable body in the proximal-to-distal direction by rotation of the distal set screw along the second rotation axis, wherein the proximal wedge and the distal wedge are configured to simultaneously distract the superior and inferior endplates in a parallel manner upon simultaneous rotation of both the proximal set screw and distal set screw in a first direction and simultaneously contract the superior and inferior endplates in a parallel manner upon simultaneous rotation of both the proximal set screw and distal set screw in a second direction opposite the first direction, wherein the proximal set screw is configured to urge the proximal wedge towards the proximal end of the expandable body in the proximal-to-distal direction upon independent rotation of the proximal set screw in the first direction, thereby distracting the superior and inferior endplates at the proximal end of the expandable body, and wherein the distal set screw is configured to urge the distal wedge towards the distal end of the expandable body in the proximal-to-distal direction upon independent rotation of the distal set screw in the first direction, thereby distracting the superior and inferior endplates at the distal end of the expandable body.

* * * * *